(12) United States Patent
Kopelman

(10) Patent No.: US 9,763,758 B2
(45) Date of Patent: Sep. 19, 2017

(54) VIRTUAL AND PHYSICAL DENTAL MODELS OF DENTAL SURFACES AND ANALOG SOCKET STRUCTURE OF A DENTAL IMPLANT AND RELATED PROCEDURES

(75) Inventor: Avi Kopelman, Palo Alto, CA (US)

(73) Assignee: Align Technology, Inc., San Jose, CA (US)

( * ) Notice: Subject to any disclaimer, the term of this patent is extended or adjusted under 35 U.S.C. 154(b) by 691 days.

(21) Appl. No.: 13/876,436

(22) PCT Filed: Jan. 12, 2012

(86) PCT No.: PCT/IL2012/050011
§ 371 (c)(1),
(2), (4) Date: Mar. 27, 2013

(87) PCT Pub. No.: WO2012/095851
PCT Pub. Date: Jul. 19, 2012

(65) Prior Publication Data
US 2013/0289950 A1    Oct. 31, 2013

Related U.S. Application Data

(60) Provisional application No. 61/432,247, filed on Jan. 13, 2011.

(51) Int. Cl.
*A61C 13/00* (2006.01)
*A61C 8/00* (2006.01)

(52) U.S. Cl.
CPC ........ *A61C 13/0004* (2013.01); *A61C 8/0001* (2013.01)

(58) Field of Classification Search
CPC ............................ A61C 13/0004; A61C 8/0001
See application file for complete search history.

(56) References Cited

U.S. PATENT DOCUMENTS 2,467,432 A    4/1949 Kesling
3,407,500 A   10/1968 Kesling
(Continued)

FOREIGN PATENT DOCUMENTS

AU    3031677 A    5/1979
AU     517102 B2    7/1981
(Continued)

OTHER PUBLICATIONS

International preliminary report on patentability dated Jul. 16, 2013 for PCT/IL2012/050011.
(Continued)

*Primary Examiner* — Kamini S Shah
*Assistant Examiner* — Jay B Hann
(74) *Attorney, Agent, or Firm* — Wilson Sonsini Goodrich & Rosati

(57) ABSTRACT

A system and method for manufacturing a physical model of a dental structure wherein the physical model is configured to allow a dental analog to be inserted into the physical model. A virtual model of the dental structure is provided including a virtual implant spatial disposition with respect to the virtual model corresponding to a physical implant spatial disposition of the dental implant. Using the virtual model, a physical model corresponding to the virtual model is manufactured, the physical model being provided with a physical analog corresponding to the virtual analog. The physical analog installation structure is configured for enabling a dental analog, corresponding to the dental implant, to be inserted. In the installed position, the dental analog has an analog spatial disposition with respect to the physical model corresponding to the physical disposition of the dental implant with respect to the physical dental structure.

22 Claims, 18 Drawing Sheets

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,866,321 A | 2/1975 | Valen |
| 3,881,251 A | 5/1975 | Valen |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,681,542 A | 7/1987 | Baum |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,931,016 A | 6/1990 | Sillard |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,123,842 A | 6/1992 | Roberts |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,234,341 A | 8/1993 | Johansen |
| 5,257,203 A | 10/1993 | Riley et al. |
| 5,273,429 A | 12/1993 | Rekow et al. |
| 5,278,756 A | 1/1994 | Lemchen et al. |
| 5,302,122 A | 4/1994 | Milne |
| 5,320,529 A | 6/1994 | Pompa |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,401,170 A | 3/1995 | Nonomura |
| 5,431,562 A | 7/1995 | Andreiko et al. |
| 5,439,380 A | 8/1995 | Marlin |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,503,557 A | 4/1996 | Sillard |
| 5,518,397 A | 5/1996 | Andreiko et al. |
| 5,527,182 A | 6/1996 | Willoughby |
| 5,528,735 A | 6/1996 | Strasnick et al. |
| 5,533,895 A | 7/1996 | Andreiko et al. |
| 5,538,424 A | 7/1996 | Gelb |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,597,303 A | 1/1997 | Simmons |
| 5,605,459 A | 2/1997 | Kuroda et al. |
| 5,607,305 A | 3/1997 | Andersson et al. |
| 5,613,852 A | 3/1997 | Bavitz |
| 5,614,075 A | 3/1997 | Andre |
| 5,621,648 A | 4/1997 | Crump |
| 5,630,717 A | 5/1997 | Zuest et al. |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,718,579 A | 2/1998 | Kennedy |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,816,810 A | 10/1998 | Antonson et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,967,783 A | 10/1999 | Ura |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,048,203 A | 4/2000 | Rosenberg |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,116,070 A | 9/2000 | Oshida et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |

(56) References Cited

U.S. PATENT DOCUMENTS

| | | |
|---|---|---|
| 6,217,334 B1 | 4/2001 | Hultgren |
| 6,227,851 B1 | 5/2001 | Chishti et al. |
| 6,227,856 B1 | 5/2001 | Beaty et al. |
| 6,244,861 B1 | 6/2001 | Andreiko et al. |
| 6,283,753 B1 | 9/2001 | Willoughby |
| 6,287,119 B1 | 9/2001 | Van Nifterick et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,322,364 B1 | 11/2001 | Oshida et al. |
| 6,350,120 B1 | 2/2002 | Sachdeva et al. |
| 6,358,052 B1 | 3/2002 | Lustig et al. |
| 6,368,108 B1 | 4/2002 | Locante et al. |
| 6,382,975 B1 | 5/2002 | Poirier |
| 6,394,809 B2 | 5/2002 | Rogers et al. |
| 6,398,548 B1 | 6/2002 | Muhammad et al. |
| 6,402,707 B1 | 6/2002 | Ernst |
| 6,468,081 B2 | 10/2002 | Yeung |
| 6,482,298 B1 | 11/2002 | Bhatnagar |
| 6,524,101 B1 | 2/2003 | Phan et al. |
| 6,554,611 B2 | 4/2003 | Chishti et al. |
| 6,558,162 B1 | 5/2003 | Porter et al. |
| 6,561,805 B2 | 5/2003 | Kumar |
| 6,572,372 B1 | 6/2003 | Phan et al. |
| 6,629,840 B2 | 10/2003 | Chishti et al. |
| 6,688,887 B2 | 2/2004 | Morgan |
| 6,705,863 B2 | 3/2004 | Phan et al. |
| 6,722,880 B2 | 4/2004 | Chishti et al. |
| 6,746,244 B2 | 6/2004 | Riley et al. |
| 6,840,770 B2 | 1/2005 | McDevitt |
| 6,857,853 B1 | 2/2005 | Tomberg et al. |
| 6,902,401 B2 | 6/2005 | Jorneus et al. |
| 6,905,336 B2 | 6/2005 | Summers |
| 6,951,460 B2 | 10/2005 | Halldin et al. |
| 7,018,207 B2 | 3/2006 | Prestipino |
| 7,033,174 B2 | 4/2006 | Giorno |
| 7,044,735 B2 | 5/2006 | Malin |
| 7,059,856 B2 | 6/2006 | Marotta |
| 7,179,089 B2 | 2/2007 | Sims et al. |
| 7,214,062 B2 | 5/2007 | Morgan |
| 7,217,130 B2 | 5/2007 | Giorno |
| 7,281,927 B2 | 10/2007 | Marotta |
| 7,287,982 B2 | 10/2007 | Riley et al. |
| 7,322,824 B2 | 1/2008 | Schmitt |
| 7,331,786 B2 | 2/2008 | Poirier |
| 7,338,286 B2 | 3/2008 | Porter et al. |
| 7,393,210 B2 | 7/2008 | Kim |
| 7,429,175 B2 | 9/2008 | Gittelson |
| 7,484,959 B2 | 2/2009 | Porter et al. |
| 7,632,095 B2 | 12/2009 | Ostman et al. |
| 7,661,956 B2 | 2/2010 | Powell et al. |
| 7,695,278 B2 | 4/2010 | Sporbert et al. |
| 7,780,448 B2 | 8/2010 | Kim |
| 7,806,691 B2 | 10/2010 | Berger |
| 7,866,980 B2 | 1/2011 | Poirier |
| 7,887,327 B2 | 2/2011 | Marotta |
| 7,959,439 B2 | 6/2011 | Bulloch et al. |
| 7,967,606 B2 | 6/2011 | Sager |
| 7,988,449 B2 | 8/2011 | Amber et al. |
| 8,007,279 B2 | 8/2011 | Bassett et al. |
| 8,011,925 B2 | 9/2011 | Powell et al. |
| 8,011,927 B2 | 9/2011 | Berckmans et al. |
| 8,021,147 B2 | 9/2011 | Sporbert et al. |
| 8,021,153 B2 | 9/2011 | Poirier |
| 8,033,826 B2 | 10/2011 | Towse et al. |
| 8,257,083 B2 * | 9/2012 | Berckmans, III .... A61C 8/0001 433/213 |
| 8,509,932 B2 * | 8/2013 | Kopelman ............ A61C 8/0001 434/172 |
| 8,651,858 B2 * | 2/2014 | Berckmans, III .... A61C 8/0001 433/24 |
| 2002/0006597 A1 | 1/2002 | Andreiko et al. |
| 2003/0009252 A1 | 1/2003 | Pavlovskaia et al. |
| 2003/0036035 A1 | 2/2003 | Chen |
| 2003/0139834 A1 | 7/2003 | Nikolskiy et al. |
| 2003/0162148 A1 | 8/2003 | Prestipino |
| 2003/0224311 A1 | 12/2003 | Cronauer |
| 2004/0128010 A1 | 7/2004 | Pavlovskaia et al. |
| 2004/0234926 A1 | 11/2004 | Halldin et al. |
| 2005/0055118 A1 | 3/2005 | Nikolskiy et al. |
| 2006/0183078 A1 | 8/2006 | Niznick |
| 2006/0286508 A1 | 12/2006 | Bassett et al. |
| 2007/0015110 A1 | 1/2007 | Zhang et al. |
| 2007/0077532 A1 | 4/2007 | Harter |
| 2007/0092854 A1 | 4/2007 | Powell et al. |
| 2007/0128580 A1 | 6/2007 | Mormann |
| 2007/0190489 A1 | 8/2007 | Riley et al. |
| 2007/0224576 A1 | 9/2007 | Ihde et al. |
| 2008/0020350 A1 | 1/2008 | Matov et al. |
| 2008/0032262 A1 | 2/2008 | Bondar |
| 2008/0153067 A1 | 6/2008 | Berckmans et al. |
| 2008/0227057 A1 | 9/2008 | Anitua Aldecoa |
| 2009/0047629 A1 | 2/2009 | Kim |
| 2009/0081613 A1 | 3/2009 | Ihde et al. |
| 2009/0104585 A1 | 4/2009 | DiAngelo et al. |
| 2009/0202963 A1 | 8/2009 | McDevitt |
| 2009/0325125 A1 | 12/2009 | DiAngelo et al. |
| 2010/0021859 A1 | 1/2010 | Kopelman |
| 2010/0086900 A1 | 4/2010 | Whipple |
| 2010/0112521 A1 | 5/2010 | Chapel |
| 2010/0112527 A1 | 5/2010 | Chapel |
| 2010/0119996 A1 | 5/2010 | Kaigler |
| 2010/0183998 A1 | 7/2010 | Poirier et al. |
| 2010/0296710 A1 | 11/2010 | Schneider et al. |
| 2010/0303316 A1 | 12/2010 | Bullis et al. |
| 2011/0117522 A1 | 5/2011 | Verma et al. |
| 2011/0129792 A1 | 6/2011 | Berckmans et al. |
| 2011/0129800 A1 | 6/2011 | Marotta |
| 2011/0183289 A1 | 7/2011 | Powell et al. |
| 2011/0200970 A1 | 8/2011 | Berckmans et al. |
| 2011/0294093 A1 | 12/2011 | Herweg et al. |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| DE | 202006017574 U1 | 3/2008 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 2009/027316 A1 | 3/2009 |
| WO | WO 2009/146164 A1 | 12/2009 |
| WO | WO 2010/108919 A2 | 9/2010 |

OTHER PUBLICATIONS

International search report dated Jul. 9, 2012 for PCT/IL2012/050011.

AADR. American Association for Dental Research, Summary of Activities, Mar. 20-23, 1980, Los Angeles, CA, p. 195.

Alcaniz, et al. "An Advanced System for the Simulation and Planning of Orthodontic Treatments," Karl HF Heinz Hohne and

(56) References Cited

OTHER PUBLICATIONS

Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space—Coded by a Laser-Projected Dot Matrix," SPIE Imaging Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," Semin. In Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Operation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/-pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays. In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does it Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).

(56) References Cited

OTHER PUBLICATIONS

Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," Am. J. Orthod., 73(1):36-46 (Jan. 1978).
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et al., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-328 (Apr. 1989).
Heaven et al., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (No. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy as One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays. Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7, 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).

(56) References Cited

OTHER PUBLICATIONS

Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue . . . The Simple, Affordable, No-Braces Treatment, Allesee Orthodontic Appliances—Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances—Pro Lab product information for patients, <http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

(56) References Cited

OTHER PUBLICATIONS

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances—Pro Lab product information for patients, 2 pages (2002).

* cited by examiner

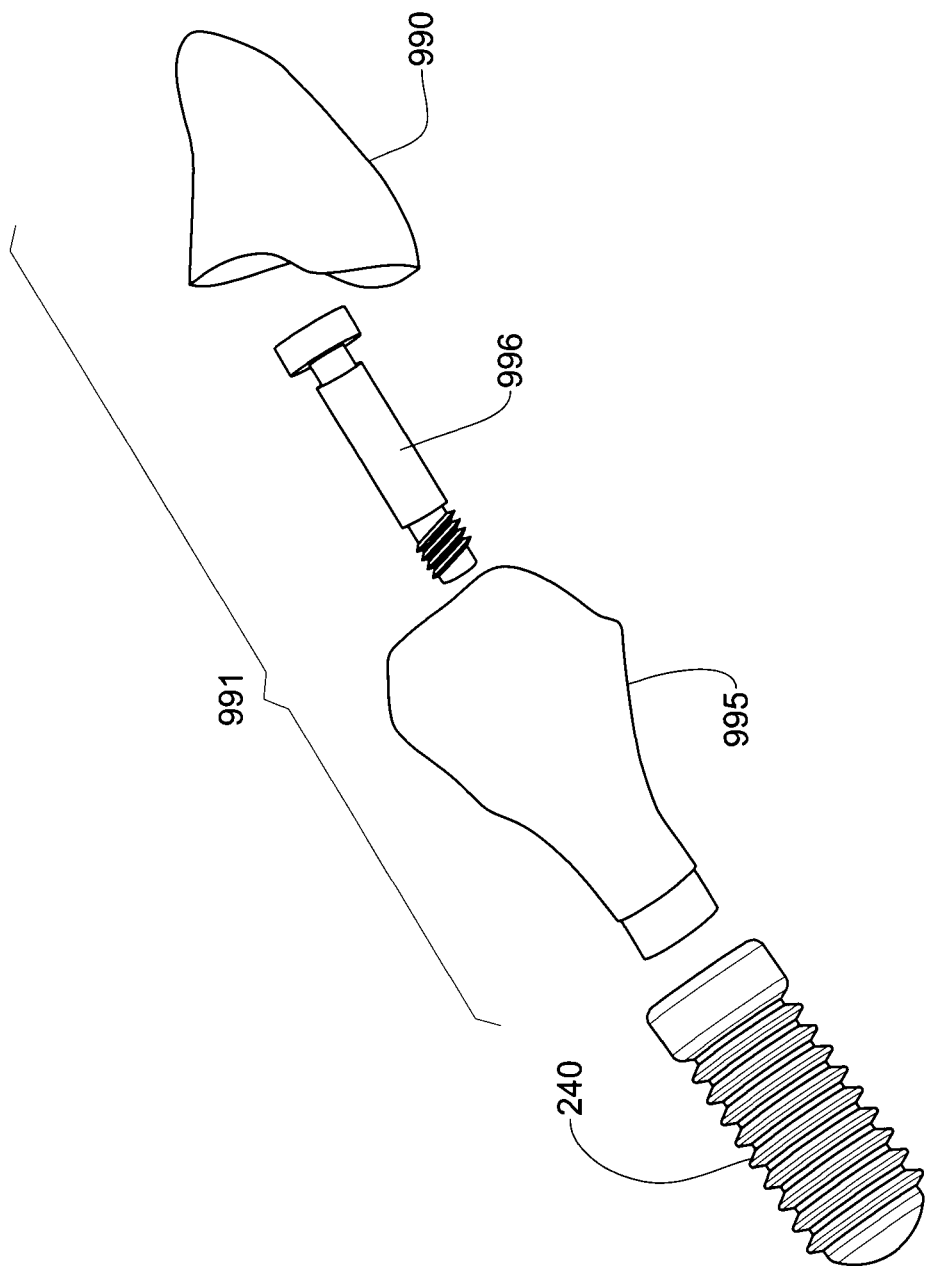

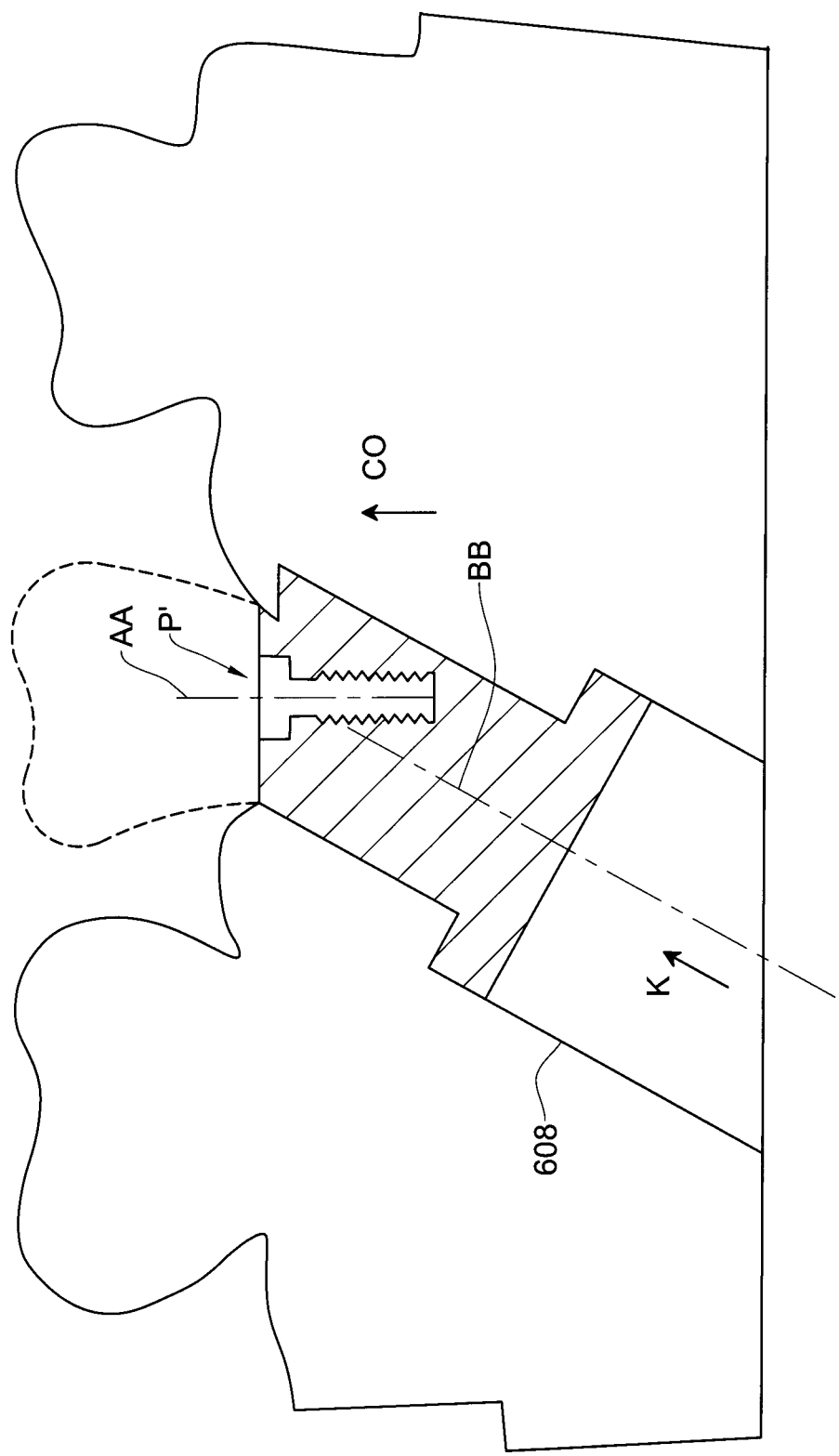

VIRTUAL AND PHYSICAL DENTAL MODELS OF DENTAL SURFACES AND ANALOG SOCKET STRUCTURE OF A DENTAL IMPLANT AND RELATED PROCEDURES

The present application is a U.S. National Phase Application under 35 U.S.C. §371 of International Application No. PCT/IL2012/050011, filed Jan. 12, 2012, which claims priority to U.S. Provisional Patent Application No. 61/432, 247, filed Jan. 13, 2011 entitled "METHODS, SYSTEMS AND ACCESSORIES USEFUL FOR PROCEDURES RELATING TO DENTAL IMPLANTS," which is incorporated herein in its entirety by reference.

The presently disclosed subject matter relates to dental implants and to dental models, in particular to methods, systems and accessories useful in procedures relating to dental implants. In particular, the presently disclosed subject matter relates to methods, systems and accessories for preparing a physical dental model for use with an analog of a dental implant, to physical models prepared in this manner, and to dental analogs for use with such physical models.

BACKGROUND

Dental implants are widely used as artificial substitutes for the root portion of missing teeth, and allow a tooth prosthesis to be securely anchored to the jaw, for example via a permanent abutment mounted to the implant. Endosseous implants generally comprise an externally threaded body, often self-taping into the bone tissues, and further comprise an internal chamber that is configured, typically internally threaded, for receiving and securing therein the anchoring stem of a permanent abutment therein.

Also well known in the art are dental analogs, each of which is a replica of a corresponding dental implant. A dental analog has an internal passage and an interface structure that are respectively identical to the internal passage and interface structure of the implant that is designed to receive, engage and secure the prosthesis and permanent abutment; however, in contrast to the dental implant, the dental analog is not intended for implantation in a human, but rather for use with a physical model of the intraoral cavity or part thereof.

Conventionally, following implantation of a dental implant in the intra oral cavity and healing of the surrounding tissues, a physical model of the intra oral cavity is often produced for facilitating design and manufacture of the permanent abutment and the prosthesis or other restoration that is to be eventually mounted onto the implant. In one procedure, an impression abutment is mounted to the implant so that it projects into the intra oral cavity, and an impression is then obtained of the intraoral cavity using well known techniques (for example, as are known in the art regarding fixture level impressions) and impression materials, for example PVS. The impression abutment can be of the pick-up type, to be embedded with the impression material and retained therein after the impression tray is removed. Alternatively the impression tray is removed without the impression abutment attached thereto, but nevertheless having a recess formed therein complementary to the outer shape of the impression abutment, enabling the transfer-type impression abutment to be mounted therein at a later time. Subsequently an analog, corresponding to the particular implant that is implanted in the patient, is attached to the impression abutment, which is in situ in the impression material, and plaster is poured into the impression tray including the analog to produce a positive plaster model of the intraoral cavity with the analog embedded. The analog is in a spatial disposition, i.e., at a position and orientation, in the plaster model corresponding to the spatial disposition of the implant in the patient's intra oral cavity. The dental technician can now attach a permanent abutment, or custom design a permanent abutment to fit the implant, and build a coping or bridge framework or prosthesis to fit into the intraoral cavity of the patient.

US 2010/0021859, assigned to the present Assignee, discloses a method and system for manufacturing a physical dental model. A virtual model is provided representative of at least a portion of the intra-oral cavity including at least one dental implant implanted therein, and the virtual model includes a virtual portion representative of each dental implant. A physical model is then manufactured based on the virtual model, the physical model including a physical analog corresponding to each implant at a respective physical spatial disposition with respect to the physical model corresponding to the respective virtual spatial disposition of the respective virtual portion with respect to the first virtual model.

By way of general background, the following publications relate to implants, analogs or to dental procedures relating to dental implants or analogs: U.S. Pat. No. 6,358,052, US 2010/0112527, US 2008/032262, US 2007/0092854, US 2006/183078, US 2003/0162148, WO 2010/108919, US 2011/294093.

Herein the "the coronal direction" with respect to a tooth refers to the direction originating from the region of the tooth root below the jaw towards the region of the crown above the jaw, while "the apical direction", refers to the direction opposite to the coronal direction.

SUMMARY

Herein "operating on" with respect to a virtual entity, for example a virtual model of the dental structure, a virtual analog installation structure, and so on, refers to conducting one or more of the following operations on the virtual entity with respect to any spatial coordinate system: translating, rotating, scaling, transforming, modifying, adding spatial data (for example adding virtual components), subtracting spatial data (for example removing, deleting or replacing virtual components).

According to a first aspect of the presently disclosed subject matter a system and a method are provided for manufacturing a physical model of a dental structure that includes a dental implant, in which a dental analog can be inserted into the physical model in a general coronal direction.

According to the first aspect of the presently disclosed subject matter there is also provided a method for creating a virtual model usable for making a physical model of a physical dental structure that includes a dental implant at an implant site, the method comprising:

using a computer system:
 (a) receiving a virtual representation of dental surfaces of the physical dental structure with dental implant data representing a location and orientation of the dental implant with respect to the dental surfaces;
 (b) receiving a virtual analog structure, the virtual analog structure being based on said dental implant; and
 (c) creating the virtual model based on:
  said virtual representation of dental surfaces; and
  a virtual analog socket structure based on said virtual analog structure and said dental implant data, and having an virtual analog insertion opening that is spaced from parts of the virtual model corresponding to dental surfaces and the implant site.

According to this aspect of the presently disclosed subject matter there is also provided a method for manufacturing a physical model of a physical dental structure that includes dental surfaces and a dental implant at an implant site, for use with a dental analog corresponding to the dental implant, the method comprising:

receiving a virtual model of the physical dental structure and a virtual analog installation structure in association with said virtual model, said virtual analog installation structure being based on the dental analog;

using said virtual model, manufacturing a physical model corresponding to said virtual model, the physical model being provided with an analog installation structure based on said virtual analog installation structure and thereby configured for enabling the dental analog to be inserted into said physical model through an insertion opening, wherein said insertion opening is spaced from a location in the physical model corresponding to the implant site in the physical dental structure.

According to this aspect of the presently disclosed subject matter there is also provided a physical model of a dental structure, the dental structure including a dental implant at an implant site, the physical model being configured for enabling insertion therein of a dental analog corresponding to the dental implant via an insertion opening that is spaced from a model implant site location on the physical model corresponding to the implant site.

According to this aspect of the presently disclosed subject matter there is also provided a dental analog configured for being inserted into a passageway of a physical model of a dental structure, which dental structure includes a dental implant at an implant site, the passageway including an insertion opening and a second opening corresponding to the implant site, said second opening having a smaller maximum width than a maximum width of said insertion opening. For example, the dental analog comprises a first analog end corresponding to said insertion opening and a second analog end corresponding to said second opening, wherein said second analog end has a smaller maximum width than a maximum width of said first analog end.

According to the first aspect of the presently disclosed subject matter a system and a method are provided for manufacturing a physical model of a dental structure that includes a dental implant, in which the physical model comprises a dental surface portion representative of the dental surfaces of the dental structure and a base portion, the physical model being configured for enabling insertion of a dental analog into the physical model via the base portion. According to the first aspect of the presently disclosed subject matter there is also provided a physical model of a dental structure that includes a dental implant, the physical model comprising a dental surface portion representative of the dental surfaces of the dental structure and a base portion, and the physical model being configured for enabling insertion of a dental analog into the physical model via the base portion.

According to a second aspect of the presently disclosed subject matter there is provided a system and method for manufacturing a composite physical dental model of a dental structure, the method comprising:

(a) providing a virtual model of the dental structure;
(b) using said virtual model, manufacturing a composite physical model corresponding to said virtual model, the physical model including a first model part and a second model part having at least one physical property different from a physical property of said first model part, wherein said first model part and said second model part are previously defined in said virtual model, and wherein said at least one physical property excludes a surface topology.

A feature of at least one example according to the first aspect and/or second aspect of the presently disclosed subject matter is that the insertion path of the physical analog is substantially independent of the topology of the dental surfaces in the vicinity of the implant site. This can facilitate installation of the respective analog for example in cases where trying to insert the analog in the physical model in an apical direction would be difficult or impossible because of potential collision with surrounding dental structures, for example, where the respective dental implant is at an awkward or shallow angle with respect to the gums and the surrounding teeth.

Another feature of at least one example according to the first aspect and/or second aspect of the presently disclosed subject matter is that the physical model in the vicinity of the opening around the analog can be defined with relatively high accuracy, since the method of installation of the analog does not require any surface detail in this part of the physical model to be disturbed, which can sometimes be the case if the analog were to be installed instead in the physical model in an apical direction.

In at least one example the physical model thus prepared according to the first aspect and/or second aspect of the presently disclosed subject matter can assist the dental technician in the design and/or preparation of the permanent abutment, coping, prosthesis and so on, in a manner known in the art. Such a prosthesis can include, for example, a custom abutment and a crown, a custom abutment and a bridge, a complete crown mounted directly to the implant, a complete bridge mounted directly to the implant, a denture, or a partial denture.

Optionally, the physical model or the composite model can be configured for mounting onto any dental articulator.

BRIEF DESCRIPTION OF THE DRAWINGS

In order to understand the presently disclosed subject matter and to see how it may be carried out in practice, examples will now be described, by way of non-limiting example only, with reference to the accompanying drawings, in which:

FIG. 1(a) illustrates in exploded view an example of prosthesis set including an abutment, prosthesis and retainer screw for the example of the dental implant of FIG. 1.

FIG. 6(g) illustrates in cross-sectional side view another variation of the dental analog example of FIG. 6(a) inserted into another variation of the example of the physical model of FIG. 5.

FIG. 14(a) illustrates in cross-sectional side view a virtual model example according to this aspect of the presently disclosed subject matter; FIG. 14(b) separately illustrates in cross-sectional side view a hard part and a soft part of composite physical model corresponding to the virtual model example of FIG. 14(a); FIG. 14(c) illustrates in cross-sectional side view the example of FIG. 14(b) with the soft part engaged with the hard part of the composite physical model example, and with the analog of the example of FIG. 6(a) accommodated at the installed position in the composite physical model example.

DETAILED DESCRIPTION

According to a first aspect of the presently disclosed subject matter there is provided a system and method for use in dental implant procedures, in particular for designing and manufacturing a physical dental model (also referred to interchangeably herein as a physical model) of a dental structure, based on and corresponding to a virtual dental model (also referred to interchangeably herein as a virtual model) of the dental structure.

Figure 1:
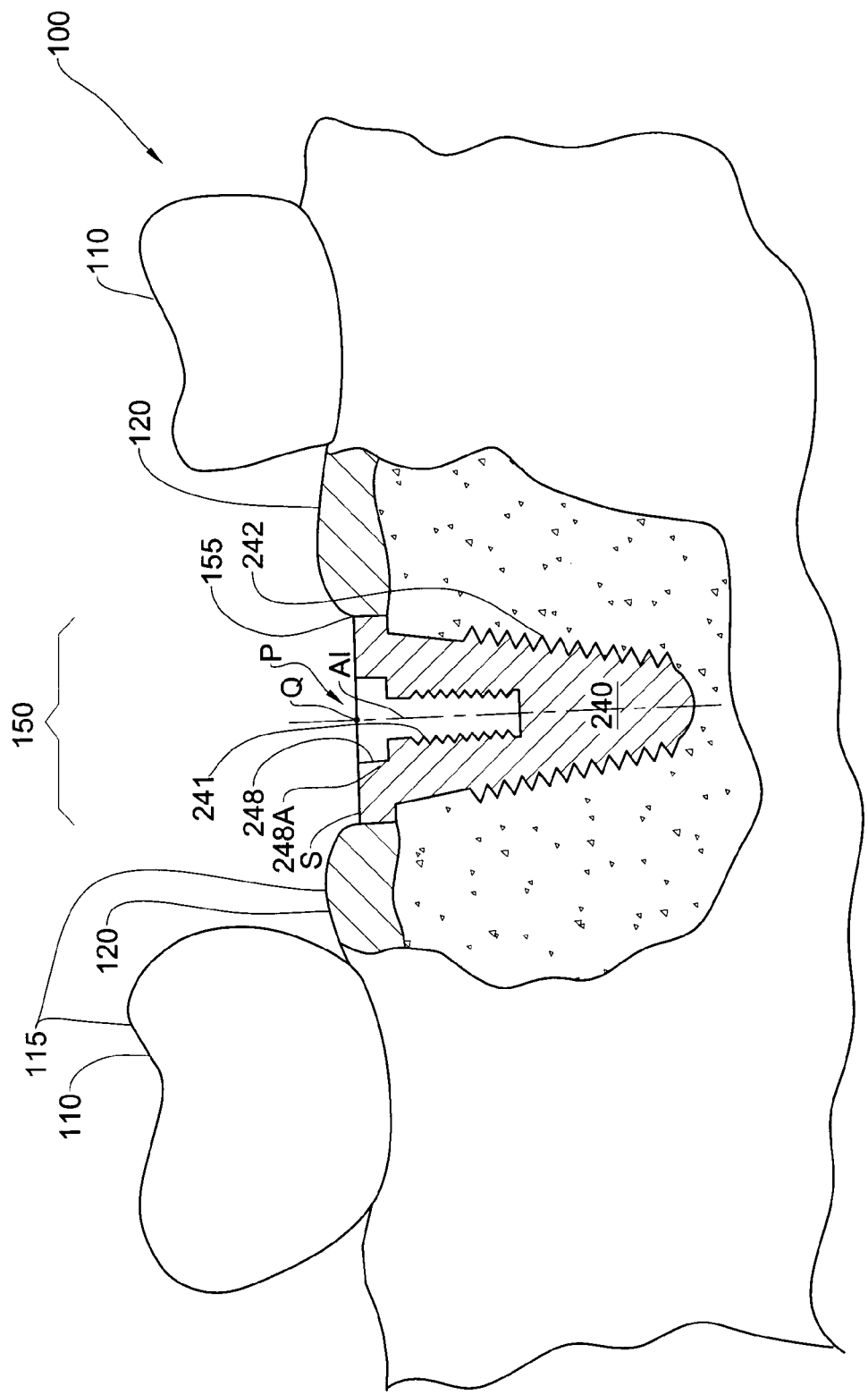
FIG. 1 illustrates in cross-sectional side view a dental structure including an example of a dental implant implanted therein in the place of a removed tooth.

Referring to FIG. 1, there is illustrated an example of such a dental structure, designated in this figure with the reference numeral 100. The dental structure 100 is part of the intra-oral cavity of a patient, in particular a visually exposed part of the intra-oral cavity of the patient, and can include partial or the full mandibular or maxillary arches, or both arches. Furthermore, the dental structure 100 includes a dental implant 240 implanted therein at a particular implant site 150, and which replaces, in part, a tooth T (FIG. 2) that was previously removed. The dental structure 100 comprises dental surfaces 115, including hard dental surfaces 110 and soft dental surfaces 120 thereof. Such hard surfaces 110 can include, for example, teeth and/or dental prostheses that are mounted to the intra-oral cavity of the patient in the vicinity of the dental implant site 150, while such soft dental surfaces 120 can include the gum, for example gingival surfaces that surround the implant. As will become clearer herein, the term "dental structure" can also refer, mutatis mutandis, to an existing physical model of the aforesaid part of the intra-oral cavity of the patient, in which a portion of the existing physical model is shaped to represent the exposed surfaces of the dental implant that is implanted in the intra-oral cavity of the patient. For example, such an existing physical model can be produced using conventional impression and casting techniques, which are well known in the art. In such an example of the dental structure 100 in the form of an existing physical model, the hard dental surfaces 110 and soft dental surfaces 120 thereof are surfaces of the existing physical model that represent the respective hard dental surfaces and soft dental surfaces of the intraoral cavity of the patient.

Referring again to FIG. 1, the dental implant 240 is illustrated in the implanted position with respect to the dental structure 100, i.e., at a particular and fixed spatial disposition P with respect to dental structure 100.

Herein, by spatial disposition P is meant the orientation and the spatial position, or the orientation and the spatial location, in 3D space of the dental implant 240 with respect to the dental structure 100, in particular with respect to some or all of the dental surfaces 115.

The dental implant 240 can comprise any suitable implant configuration that is commercially available or alternatively that is custom made. The dental implant 240 in this example comprises a prosthesis interface implant part 248 and a prosthesis engaging implant part 241, and is engaged to the dental structure 100 via an anchoring structure such as external screw threads 242. For example, prosthesis interface implant part 248 can comprise a hexagonal counterbored configuration and the prosthesis engaging implant part 241 can comprise an internally threaded well, compatible with many types of commercially available prostheses; other configurations for these components can of course be comprised, instead, in the dental implant. For example the dental implant can comprise a Morse taper connection; and/or can be configured for use with a screw retained crown or a cemented crown; and/or can be configured for straight or angulated abutments.

Referring to FIG. 1(a), an example of a prosthesis system 991 is illustrated for use with dental implant 240. In this example, the prosthesis system 991 includes a dental prosthesis 990 that can be mounted to the dental implant 240 via a permanent abutment 995 and retainer screw 996. The prosthesis interface implant part 248 and the prosthesis engaging implant part 241 mate with and engage to a complementary structure in the dental prosthesis 990 and/or permanent abutment 995.

While the following examples are each directed to a case of a single implant implanted in the dental structure, it is readily appreciated that the system and method are readily applicable in a similar manner, mutatis mutandis, to cases in which there is a plurality of implants that can be implanted in the intraoral cavity of a patient, whether the implants are independent from one another, each being used for a separate prosthesis, or whether at least some of the implants are to be coupled to be used together for a single bridge prosthesis or other multiple tooth prostheses, dentures, etc., for example.

As will become readily apparent, corresponding to the dental structure 100, a physical dental model is manufactured according to the first aspect of the presently disclosed subject matter including physical model surfaces that are representative of at least some of the hard dental surfaces 110 and soft dental surfaces 120 of the dental structure 100.

As will also become readily apparent, in at least some examples of the physical model, the physical model includes a passageway having an analog insertion opening in the physical model, for example at a base thereof. The passageway and analog insertion opening are configured to allow a dental analog, corresponding to the dental implant, to be installed into the physical model in an insertion path along an insertion direction, to an installed position in the model.

In at least some examples, the insertion direction is referred to herein as the respective general coronal direction K, as defined below, and is fixed for a particular set of: (a) a physical model and (b) the form or design of the corresponding analog. Referring again to FIG. 1, in some cases, where the dental implant is implanted having its axis AI parallel or close to the coronal direction CO, the insertion direction for the corresponding implant, i.e., the respective general coronal direction, can also be parallel or near parallel to coronal direction CO. On the other hand, there are specific cases where the implant has been implanted in a spatial disposition with respect to the dental structure where the axis AI is inclined at a relatively large acute angle to the coronal direction CO. In such cases, and depending on the design of the dental implant, the insertion direction for the implant, i.e., the respective general coronal direction, can also be relatively large acute angle to coronal direction CO.

In the installed position, the analog is coupled to the physical model in a relative spatial disposition (i.e., at a spatial position/location and orientation in 3D space) with respect to the physical model that corresponds to and replicates the relative spatial disposition between the dental implant and the dental structure. As will become readily apparent, the passageway is first modeled in the corresponding virtual dental model of the dental structure, which in turn enables the physical passageway in the physical model to be manufactured.

Figure 2:
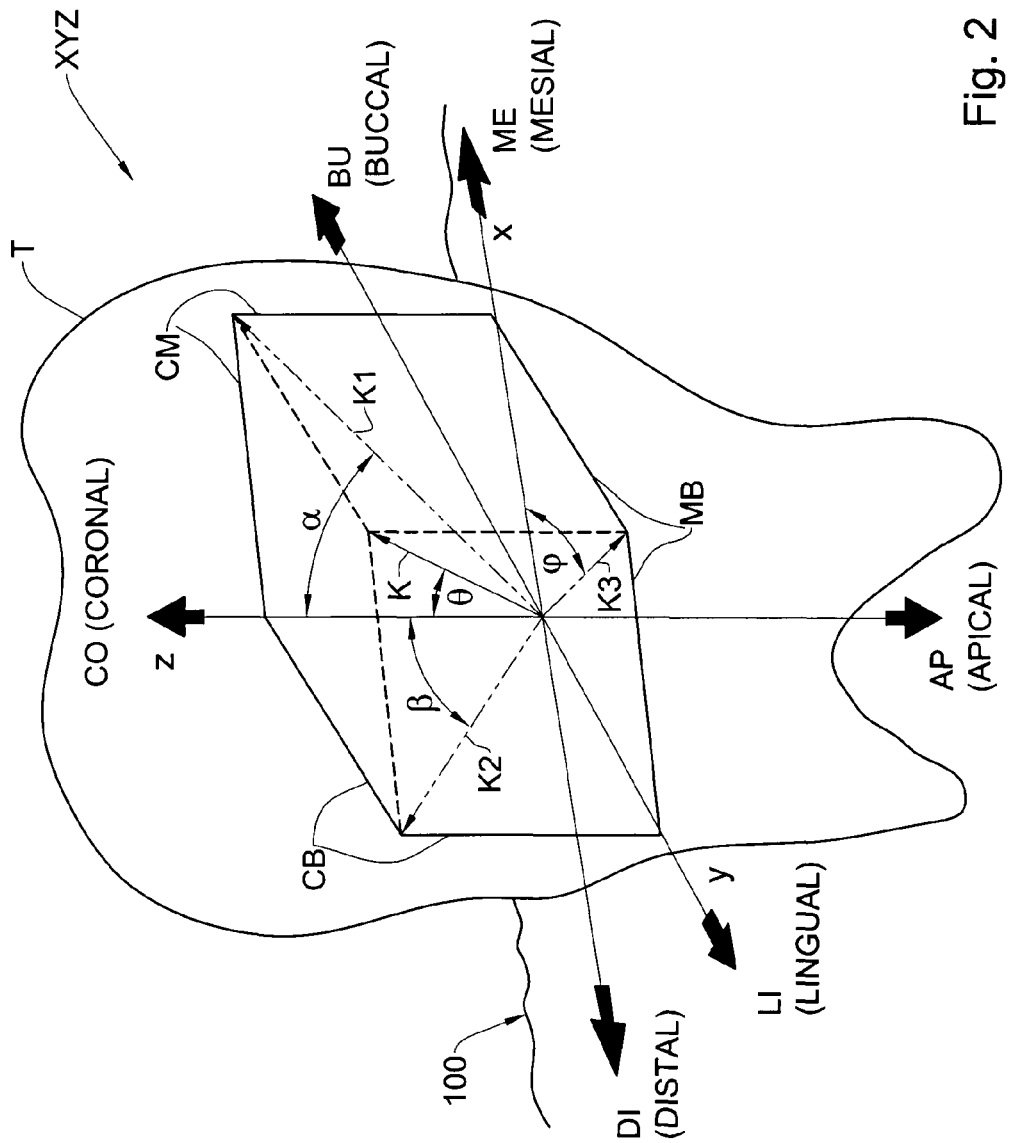
FIG. 2 schematically illustrates an example of a general coronal direction with respect to a spatial coordinate system referenced to the removed tooth and dental structure of FIG. 1.

Referring to FIG. 2, an example of a general coronal direction K is illustrated with respect to six directions along three orthogonal axes x, y, z of a spatial coordinate system. The spatial coordinate system is, in this example, Cartesian coordinate system XYZ, and is referenced to the removed tooth T and with respect to the original location of tooth T in the dental structure 100. The aforesaid six directions include: the true coronal direction CO and the true apical direction AP the removed tooth T, along the z-axis; the mesial direction ME and the distal direction DI the removed tooth T, along the x-axis; and the buccal direction BU and the lingual direction LI the removed tooth T, along the y-axis.

The "true coronal direction", used herein synonymously with "the coronal direction", refers to the direction originating from the region of the tooth root within the jaw and extending towards the region of the crown above the jaw, with reference to the tooth T and with respect to the original location of tooth T in the dental structure 100, at or near the current implant site 150. Since teeth are sometimes crooked, the true coronal direction CO (and thus the orientation of the respective Cartesian coordinate system XYZ) relative to the jaw can vary between one tooth and another in the same jaw. The "true apical direction", used herein synonymously with "the apical direction", refers to the direction opposite to the true coronal direction.

A mesial-buccal plane MB can be defined, aligned with the mesial direction ME and the distal direction DI on the one hand, and the buccal direction BU and lingual direction LI on the other hand, i.e., the x-y plane.

Similarly, a coronal-buccal plane CB can be defined, aligned with the true coronal direction CO and true apical direction AP on the one hand, and the buccal direction BU and lingual direction LI on the other hand, i.e., the z-y plane.

Similarly, a coronal-mesial plane CM can be defined, aligned with the true coronal direction CO and true apical direction AP on the one hand, and the mesial direction ME and distal direction DI on the other hand, i.e., the z-x plane.

It is to be noted that by "general coronal direction" K is meant any direction having a directional vector that can be angularly displaced from the true coronal direction CO in 3D space by a total angular displacement with respect to the true coronal direction CO not greater than 90°. The term "general coronal direction" thus includes any direction having a directional vector including at least one directional component thereof aligned with true coronal direction CO. Additionally or alternatively, "general coronal direction" is meant any direction having a directional vector that excludes having any directional component thereof aligned with true apical direction AP, i.e., along a non-apical direction.

The aforesaid total angular displacement, designated as angle $\theta$ in FIG. 2, can have a first angular component, angle $\alpha$, and/or a second angular component, angle $\beta$.

For example, the first angular component, angle $\alpha$, can be defined as the angular disposition of a first projection K1 of the general coronal direction K on the coronal-mesial plane CM, taken with respect to the true coronal direction CO and towards the meisal direction ME (or instead taken with respect to the true coronal direction CO and towards the distal direction DI).

For example, the second angular component, angle $\beta$, can be defined as the angular disposition of a second projection K2 of the general coronal direction K on the coronal-buccal plane CB, taken with respect to the true coronal direction CO and towards the lingual direction LI (or instead taken with respect to the true coronal direction CO and towards the buccal direction BU).

Alternatively, one or the other of the first angular component and the second angular component can be replaced with a third angular component, angle $\phi$. Angle $\phi$ can be defined as the angular disposition of a third projection K3 of the general coronal direction K on the mesial-buccal plane MB, taken with respect to the meisal direction ME and towards the lingual direction LE (or towards the buccal direction BU), or indeed taken with respect to the distal direction DI and towards the lingual direction LI or towards the buccal direction BU.

In at least one example, angle α can be zero, so that the general coronal direction K lies on the coronal-buccal plane CB. In at least one example angle β can be zero, so that the general coronal direction K lies on coronal-mesial plane CM. In at least one example, angle α and angle β can both be zero, so that the general coronal direction K is parallel or aligned with the true coronal direction CO.

It is readily apparent that the first angular component, angle α, and the second angular component, angle β, can be defined on any desired first and second different but mutually-orthogonal planes that include the coronal direction CO, such planes being optionally different from the coronal-mesial plane CM or the coronal-buccal plane CB. This automatically defines a third angular component of the absolute angular displacement along a third plane orthogonal to the first and second planes.

It is also readily apparent that the total angular displacement, angle θ, between the general coronal direction K and the true coronal direction CO can be defined with respect to any suitable spatial coordinate system other than the Cartesian coordinate system XYZ. For example, the total angular displacement, angle θ, can be defined with respect to a spherical coordinate system, referenced to the coronal-apical z-axis and the mesial-buccal plane MB, and thus via a respective elevation and a respective azimuth corresponding to the general coronal direction K.

By way of non-limiting example, the total angular displacement, angle θ, between the general coronal direction K and the true coronal direction CO is fixed for a particular physical model and corresponding analog to be used therewith, and can be any specific angle in the range from 0° to 90°, or in the range from 0° to about 60°, or in the range from 0° to about 45°, or in the range from 0° to about 30°, or in the range from 0° to about 20°, or in the range from 0° to about 10°, or in the range from 0° to about 5°, or in any other range between 0° and 90°.

Thus, as will become readily apparent, in at least some examples the general coronal insertion direction K of the dental analog with respect to the physical model can be such as to provide an insertion path into the physical model that is aligned with a longitudinal axis of the dental analog, for example, even in cases where the corresponding longitudinal axis of the respective dental implant is severely displaced angularly from the true coronal direction CO.

As will become readily apparent, in at least some examples, the respective analog is inserted into the corresponding physical model in a direction opposite to the direction in which the dental implant is installed in the corresponding dental structure.

As will also become readily apparent, in at least some examples, the respective analog is inserted into the corresponding physical model in a direction passing through a part of the physical model representative of dental surfaces 115, from a first location with respect to the physical model corresponding to an inside of the dental structure to a second location with respect to the physical model corresponding to an outside of the dental structure.

As will also become readily apparent, in at least some examples of the aforesaid method and system, the general coronal insertion direction K for an analog with respect to the respective physical model provides an insertion path into the physical model for the implant that inherently avoids collision with at least model dental surface parts of the physical model that represent the real dental surfaces of the dental structure 100. In particular, such collision is avoided with respect to model dental surface parts that represent the hard dental surfaces in proximity to the dental implant, for example the teeth adjacent to the implant. Furthermore the insertion path can be such as to avoid having to disturb other parts of the physical model, for example the model dental surface parts thereof that reproduce the soft dental surfaces 120 of the dental structure 100 that are in abutting relationship with the dental implant 240, for example the gingival surfaces that surround the implant.

Referring again to FIG. 1, the spatial disposition P of the implant 240, i.e., the spatial position and orientation in 3D space, with respect to the dental structure 100, can be defined in many different ways. For example, spatial disposition P can be defined via the spatial orientation of longitudinal axis AI of the dental implant 240 with respect to any chosen coordinate system, together with the spatial position of a point Q associated with the dental implant 240 (i.e., having a defined spatial relationship to the dental implant 240) and which is at a fixed spatial relationship to the longitudinal axis AI. For example, point Q may be the intersection point between a plane S and longitudinal axis AI, wherein plane S is coplanar with the coronal-facing face 248A of prosthesis interface implant part 248. Such a chosen coordinate system is the same coordinate system as may be used for the dental structure 100, or alternatively has a known and fixed spatial relationship with another coordinate system used for the dental structure 100.

Figure 4:
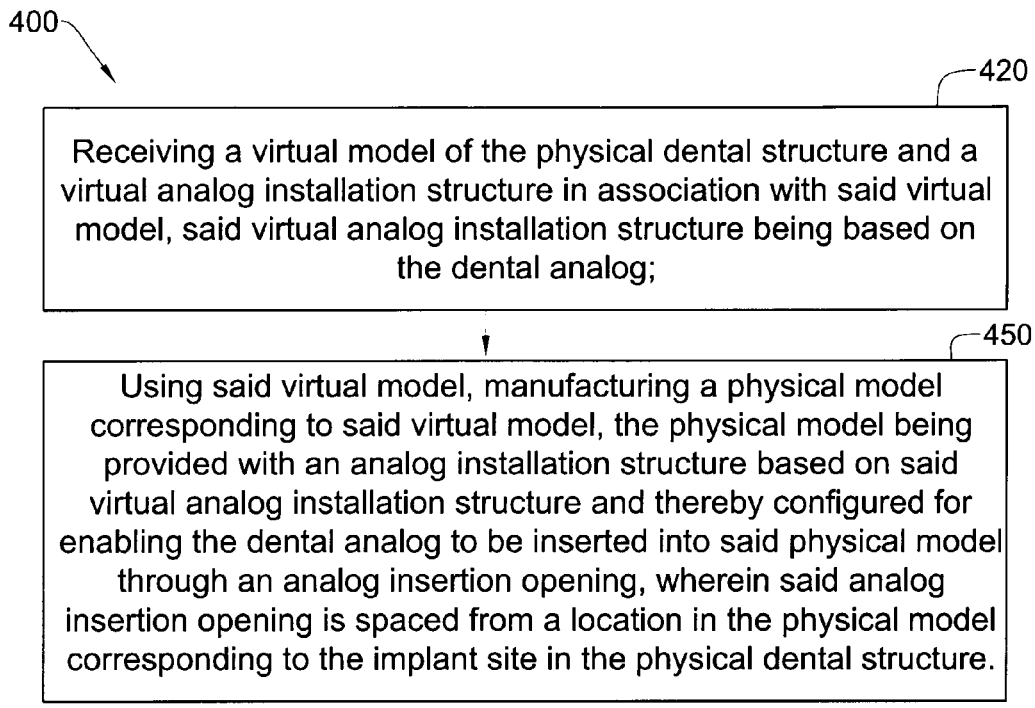
FIG. 4 is a schematic illustration of an example of a method according to a first aspect of the presently disclosed subject matter.
Figure 5:
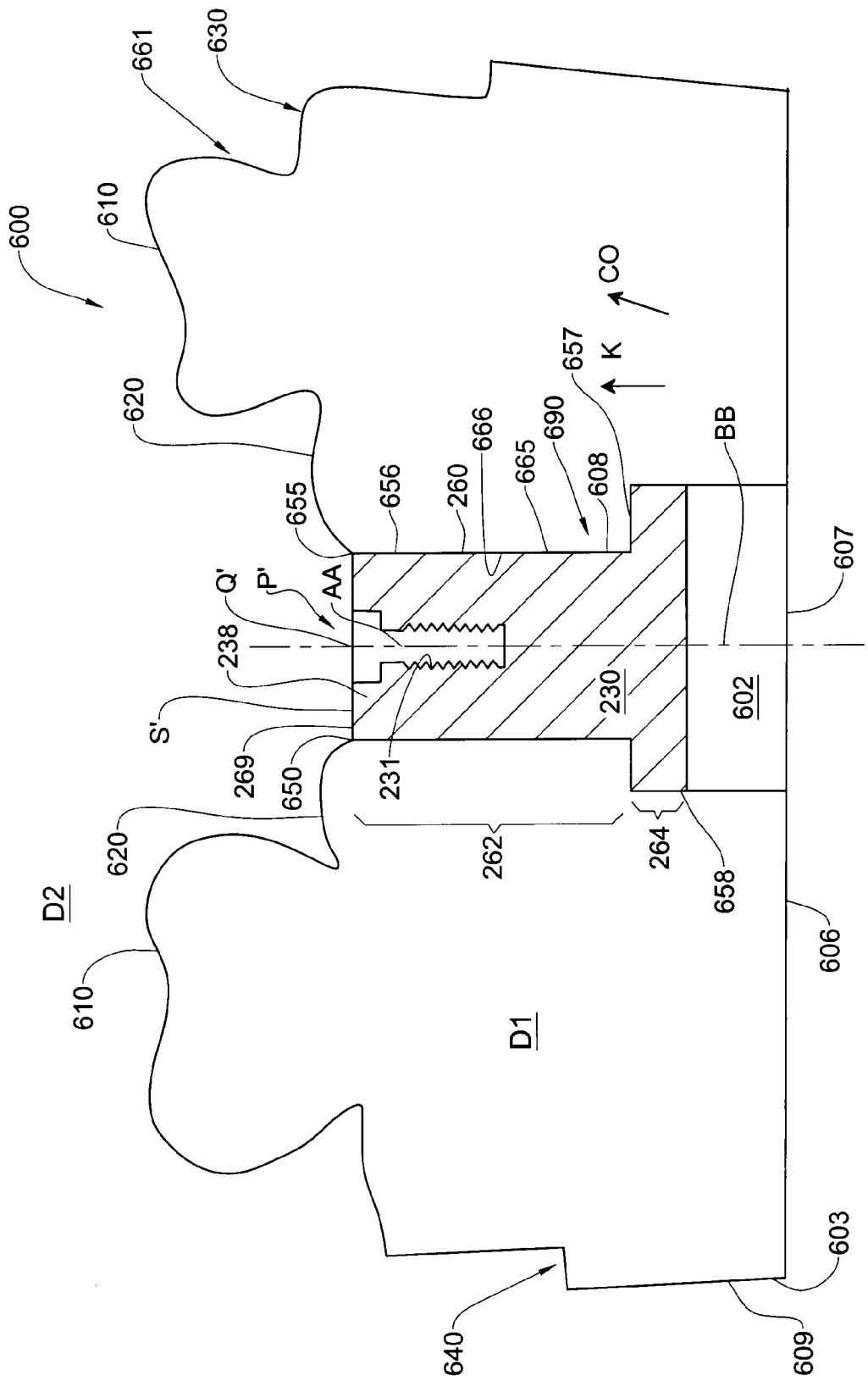
FIG. 5 illustrates in cross-sectional side view an example of a dental model corresponding to the dental structure of FIG. 1 and including a corresponding example of a dental analog inserted therein.

Referring to FIG. 5, there is illustrated a first example of a physical model 600, configured for enabling a first example of the analog 230 to be installed therein via an analog insertion opening 607 (in a respective general coronal direction K) to an installed position at a spatial disposition P' with respect to the physical model 600. As will be disclosed in greater detail below, and referring to FIGS. 4 and 3, physical model 600 is manufactured according to method 400, for example using system 200.

Figure 6A:
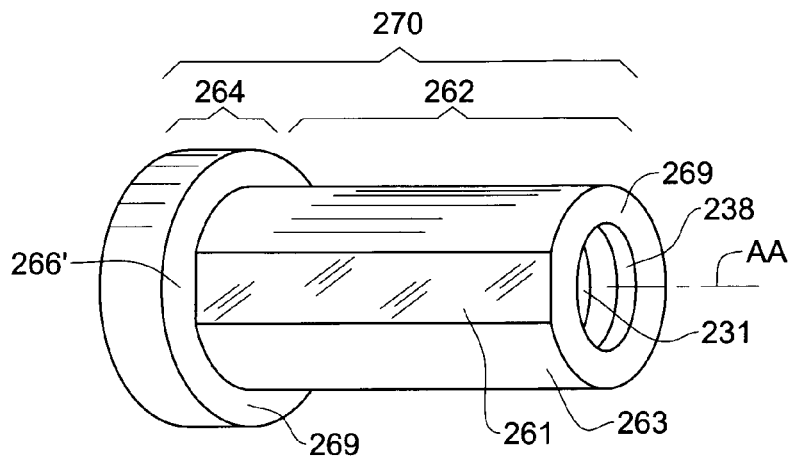
FIG. 6(a) illustrates in isometric view the dental analog example of FIG. 5.

In FIG. 5, the dental analog 230 is illustrated in the installed position with respect to physical model 600, at a spatial disposition P', the dental analog 230 corresponding to and essentially being, in a functional sense with respect to the respective prosthesis system 991, for example, a replica of the dental implant 240. Referring also to FIG. 6(a), the dental analog 230 comprises, at a coronal end thereof, a prosthesis interface analog part 238 having coronal-facing face 269, and a prosthesis engaging analog part 231 that correspond to and are essentially identical to the prosthesis interface implant part 248, coronal-facing face 248A and the prosthesis engaging implant part 241, respectively. The dental analog 230 also comprises a longitudinal axis AA corresponding to longitudinal axis AI of the dental implant 240, wherein longitudinal axis AA has the same spatial relationship with respect to prosthesis interface analog part 238 and to the prosthesis engaging analog part 231 as longitudinal axis AI has with respect to the prosthesis interface implant part 248 and the prosthesis engaging implant part 241, respectively. Thus, the longitudinal axis AA is aligned with respect to the prosthesis interface analog part 238 and the prosthesis engaging analog part 231 of the analog 230, i.e., aligned with the centerline of the prosthesis engaging analog part 231, and not necessarily with a centerline referenced to the external form 270 of the dental analog 230.

Spatial disposition P' with respect to the installed analog 230 at the installed position in the physical model 600 can be defined in any suitable manner, for example in a similar manner to spatial disposition P, mutatis mutandis. For example, spatial disposition P' can be defined via the spatial orientation of longitudinal axis AA with respect to any chosen spatial coordinate system, together with the spatial position of a point Q' associated with the analog 230 and which is at a fixed spatial relationship to the longitudinal axis AA. For example, point Q' can correspond to point Q of the dental implant 240, and can be the intersection point between a plane S' and longitudinal axis AA, wherein plane S is coplanar with the coronal-facing face 269 of prosthesis interface analog part 238. Such a chosen coordinate system is the same coordinate system as may be used for the physical model 600, or has a known and fixed spatial relationship with another coordinate system used for the physical model 600.

The external form 270 of the dental analog 230 is not configured for implantation in a human, but rather for coupling with the corresponding physical model 600, at a spatial disposition P' with respect thereto that replicates the spatial disposition P of the dental implant 240 with respect to dental structure 100 (see also FIG. 1). In particular, in this example, and referring again to FIGS. 5 and 6(a), the external form 270 of the dental analog 230 comprises a coronal portion 262 adjacent an enlarged apical portion 264. The coronal portion 262 has a maximum width that is smaller than a maximum width of the enlarged apical portion 264. In this example, the enlarged apical portion 264 having a larger cross-sectional area than a cross-sectional area of the coronal portion 262. In at least some alternative variations of this example, the enlarged apical portion 264 can instead have a portion thereof that projects laterally with respect to the outer surface of the coronal portion 262.

Referring in particular to FIG. 6(a), the coronal portion 262 comprises a generally cylindrical outer surface 263 about axis AA and that is made asymmetrical via a flat portion 261. The flat portion 261 extends along the longitudinal length of the coronal portion 262 from coronal-facing face 269 to the coronal face 265 of enlarged apical portion 264, the coronal face 265 being defined on a plane substantially orthogonal to axis AA. The enlarged apical portion 264 acts as mechanical stop arrangement which abuts shoulder 657 formed in the physical model 600 to define the limit of penetration of the analog 230 into the physical model 600 in the respective general coronal direction K to the installed position. The enlarged apical portion 264, in this example, is generally cylindrical and symmetrical about axis AA, but can instead have any other symmetrical shape about axis AA or any other axis, or can have an asymmetrical shape if desired.

Referring again to FIG. 5, the first example of physical model 600 comprises a model dental surface part, also referred to as first model part 630, including an outer model surface 661 representing dental surfaces of the dental structure 100 that are exposed in the dental structure 100, and a second model part 640 including an analog installation structure 690. Herein, "analog installation structure" is used interchangeably with "physical analog socket structure".

Referring to FIG. 1 and FIG. 5, the first model part 630, and in particular the outer model surface 661, includes parts 610 that correspond to the hard surfaces 110, and parts 620 that correspond to the soft surfaces 120. The first model part 630 also comprises a coronal opening 650 having a perimeter 655 corresponding to the interface 155 between the soft surface 120 and the implant 240 at implant zone 150 of the dental structure 100.

Referring to the second model part 640, the analog installation structure 690 is configured for enabling the analog 230 to be inserted into the model 600 in a respective general coronal direction K to an installed position at spatial disposition P' with respect to the model 600 that replicates the spatial disposition P of the dental implant 240 with respect to the dental structure 100. In the installed position, all or part of coronal-facing face 269, prosthesis interface analog part 238, and prosthesis engaging analog part 231 of the analog 230 are exposed via the coronal opening 650. This allows a prosthesis system (e.g., comprising dental prosthesis 990, permanent abutment 995 and retainer screw 996, see FIG. 1(a)) to be mounted to the analog 230 with respect to the physical model 600, in a manner comparable to that intended for the dental implant 240 in the dental structure 100.

The second model part 640 further comprises a physical model base 609 having a base surface 603 and defining an apical portion 606. In this example the base 609 has a length and breadth greater than the overall length and breadth, respectively, of the outer model surface 661, though in alternative variations of this example the length and/or breadth of the model base 609 can be the same as or less than the respective length and/or breadth of the outer model surface 661.

In this example the base 609 has a height extending in an apical direction away from the outer model surface 661. In this connection the length and breadth dimensions can be taken along directions orthogonal to the apical-coronal (height) direction. In alternative variations of this example, the model base can be relatively thin or nominal, for example formed by a projection of the outer model surface 661 to a plane, for example orthogonal to the apical direction.

Analog installation structure 690 comprises a passageway 608 extending in a general coronal direction K from analog insertion opening 607, formed in apical portion 606, to coronal opening 650. The coronal opening 650 is also referred to herein as an access opening to the installation structure 690, located at a location in the physical model corresponding to the location of the implant site 150. The coronal opening 650 is also referred to herein as an auxiliary opening.

The passageway 608 is elongate, defining a passageway longitudinal axis aligned with said general coronal direction, and in this example of the analog 230, the passageway longitudinal axis BB is co-axial with a longitudinal axis AA of analog 230 when the analog 230 is in the installed position therein. It is to be noted that in other examples of the analog 230, the passageway longitudinal axis is not necessarily co-axial or even parallel with a longitudinal axis AA of the analog when the analog is in the installed position therein.

It is readily apparent that analog insertion opening 607 is spaced from the parts of the physical model corresponding to the implant site 150, in particular that analog insertion opening 607 is spaced from coronal opening 650. It is also readily apparent that analog insertion opening 607 is different from coronal opening 650.

In at least some examples the analog insertion opening 607 is spaced from the outer model surface 661. In at least some examples the analog insertion opening 607 is at a location other than the outer model surface 661. In at least some examples the analog insertion opening 607 excludes a location in parts of the physical model corresponding to the implant site 150.

In particular, the passageway 608 is configured, for example via the shape of its internal walls 666, for enabling the analog 230 to be inserted into the physical model 600 in the respective general coronal direction K to the respective installed position, and defines an analog chamber 665 at the coronal end of passageway 608 for accommodating the analog 240 at the installed position, at spatial disposition P' with respect to the physical model 600. The precise form of the second model part 640, and in particular of the analog installation structure 690, thus depends on the particular external configuration of the analog 230, i.e., the external form 270 thereof. Thus, in this example, passageway 608 comprises: a first passageway portion 656 having an internal surface that is complementary to the outer surface 263 and including a corresponding passageway flat portion (not shown) that is complementary to analog flat portion 261; a shoulder 657 that is complementary to face 265; and a second passageway portion 658 having and internal surface that is complementary to the outer surface of enlarged apical portion 264 and extends in a general apical direction A to opening 607.

In the installed position, analog 230 forms a tight fit with passageway 608, and in particular with analog chamber 665, and this fixes the position of the analog 230 in the physical model 600 in four degrees of freedom, preventing translation along, or rotation about, two orthogonal axes that are also orthogonal to the respective general coronal direction K, and thus also to the longitudinal axis BB, and in this example also with respect to the longitudinal axis AA.

The asymmetry of coronal portion 262, in particular the analog flat portion 261, ensures that the analog 230 can be inserted into passageway 608, and in particular into analog chamber 665, in only one angular disposition about the respective general coronal direction K, and thus also about longitudinal axis BB with respect to the passageway 608. In this installed position the analog flat portion 261 is in contact with the corresponding passageway flat portion, and furthermore such contact further prevents rotation between the analog 230 and the physical model 600 about the respective general coronal direction K, and thus also about longitudinal axis BB. Furthermore, abutment between the coronal face 265 and the shoulder 657 provides a mechanical stop in the general coronal direction K, and thus ensures that the analog 230 can be inserted into passageway 608 to a particular depth along the respective general coronal direction K, and such contact prevents further coronal translation by the analog 230 into the physical model 600 along the respective general coronal direction K, and thus also along longitudinal axis BB. The analog 230 can be prevented from translating in the general apical direction out of the installed position in any number of ways, for example by providing a suitable adhesive or a friction fit between the analog 230 and passageway 608, or filling the apical end 602 of the passageway with a suitable filler or plug, and so on.

In at least this example, the insertion path into passageway 608 passageway 608 is defined by (and aligned with) the desired spatial orientation of the axis AA of the analog 230 at the installed position with respect to the physical model 600, which in turn matches the spatial orientation of the axis AA of the dental implant 240 with respect to the dental structure 100. It is also readily evident that the longitudinal position of the shoulder 657 with respect to the outer model surface 661 and with respect to longitudinal axis AA is such as to ensure that point Q' of the analog 230 (in the installed position) is at a position with respect to the outer model surface 661 that replicates point Q of the dental implant 240 with respect to the dental structure 100.

With the dental analog 230 thus fixed in six degrees of freedom with respect to the physical model 600 in spatial disposition P' replicating the geometrical relationship between the dental implant 240 and the dental structure 100, a prosthesis system (e.g., prosthesis system 991, see FIG. 1(a)) can be designed and/or tested using the dental analog 230 while coupled to the physical model 600, and enabling the prosthesis system to be subsequently mounted to the patient via the dental implant 240.

In this example, the implant site 150, in particular the perimeter 655 of coronal opening 650 has a shape and dimension complementary to the shape and outer diameter of the coronal-facing face 269. Alternatively, the coronal opening 650 may laterally overlap the periphery of the coronal-facing face 269 but it is not desired for this overlap to act as a mechanical stop and thus limit or define the relative position between the analog 230 and the passageway 608: for example, and as will be described in greater detail below, the physical model may be manufactured as a composite model in which part of the physical model in the vicinity of and overlapping the periphery of the coronal-facing face 269 may be made of a soft material, unsuitable or undesirable for acting as a mechanical stop in the general coronal direction for the analog 230.

In the example illustrated in FIG. 5 and FIG. 6(a), the respective general coronal direction K is shown as being oriented close to the orientation of the respective coronal direction CO of the removed tooth. Nevertheless, the example of dental analog 230 illustrated in these figures can also be used in situations wherein the dental implant 240 is implanted in the dental structure 100 at a spatial disposition P having a relatively large angular displacement with respect to the respective coronal direction. FIG. 6(e) illustrates an example of such a situation in which the analog 230 is at a corresponding angular disposition P', where the respective general coronal direction K and the passageway axis BB are angularly displaced from the respective coronal direction CO of the removed tooth by a correspondingly (though not necessarily identical) relatively large acute angle, marked λ in this figure. In cases such as illustrated in FIG. 6(e), the analog and corresponding implant can be configured for use with an angulated abutment and prosthesis (marked 990') to match the orientation of the prosthesis to the adjacent teeth and to provide the correct occlusion with the teeth of the opposite jaw. On the other hand, and as illustrated in FIG. 6(f), an alternative design for the analog can be provided with respect to the case of FIG. 6(e), in which, the spatial disposition P' of the analog 230 represents the spatial disposition of the implant with respect to the dental structure having a relatively large angular displacement with respect to the respective coronal direction CO. In the example of FIG. 6(f), the respective dental analog is configured to be inserted into the physical model along a respective general coronal direction K that is parallel or close to parallel with respect to the coronal direction, with the analog having a reference longitudinal axis that is parallel to the passageway longitudinal axis BB, and parallel with the general coronal direction K, but angularly displaced with respect to the corresponding axis AA of the analog.

It is therefore apparent that for any given configuration of a dental implant, implanted at a particular spatial disposition P, a variety of different analogs can be provided, all such analogs having the same prosthesis-engaging configuration corresponding to the prosthesis engaging interface of the implant, but having different external forms 270 which are, in turn, configured for different configuration of the respective installation structure 690 of the respective physical model 600. Thus, in alternative variations of these examples, the analog 230 and the analog installation structure 690 of the physical model 600 may have different configurations to ensure that dental analog 230 is fixed in six degrees of freedom with respect to the physical model 600 in spatial disposition P', while enabling insertion of the analog 230 into the physical model 600 in the general coronal direction K for example.

Figure 6B:
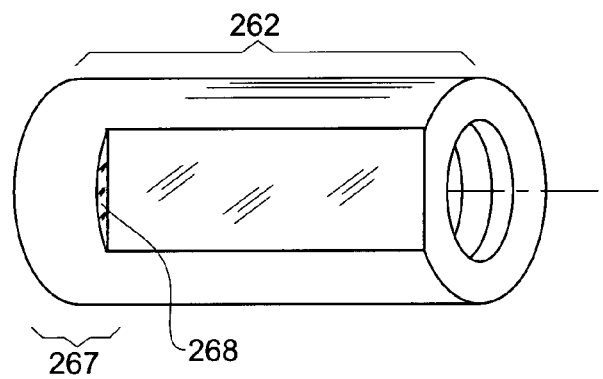
FIG. 6(b) to 6(d) respectively illustrate in isometric view alternative variations of the dental analog example of FIG. 6(a)

For example, referring to FIG. 6(b), the enlarged apical portion 265 of the example of FIG. 6(a) is omitted from the analog 230, and the analog flat portion 261 does not extend to the apical end of the coronal portion 262, but rather to a location coronally displaced therefrom, thus forming a coronal face 268 displaced from the apical end 267 of the coronal portion 262. Correspondingly, passageway 608 is formed in physical model 600 with a shoulder complementary to coronal face 268 (and can thus omit shoulder 657), and thus defines the longitudinal position of the implant 230 in the passageway 608 and thus with respect to the physical model 600 in a manner similar to that provided by the coronal face 265 and the shoulder 657 of the example illustrated in FIGS. 5 and 6(a), mutatis mutandis.

Figure 6C:
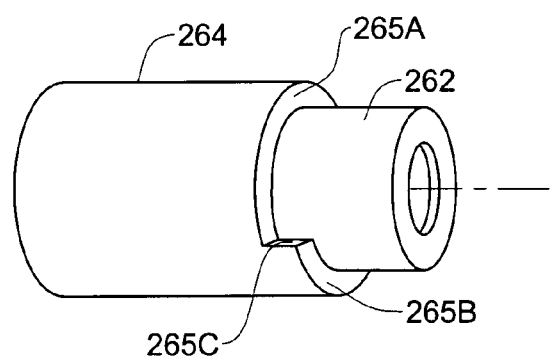

In another example, referring to FIG. 6(c), the analog flat portion 261 of the example of FIG. 6(a) can be omitted from the analog 230, and the enlarged apical portion 264 comprises instead a coronal face having two portions 265A, 265B both orthogonal to respective general coronal direction K, and thus also to longitudinal axis AA, but axially displaced from one another via joining walls 265C. Correspondingly, passageway 608 is formed with a stepped shoulder configuration (rather than shoulder 657), comprising two shoulders complementary to portions 265A, 265B, and which thus defines the longitudinal position of the implant 230 in the passageway 608 and the angular orientation of the implant with respect to the physical model 600 about respective general coronal direction K, and thus also about longitudinal axis AA.

Figure 6D:
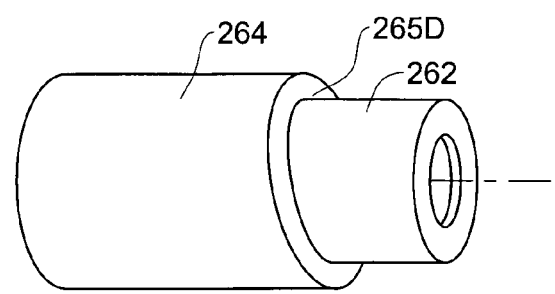
Figure 6E:
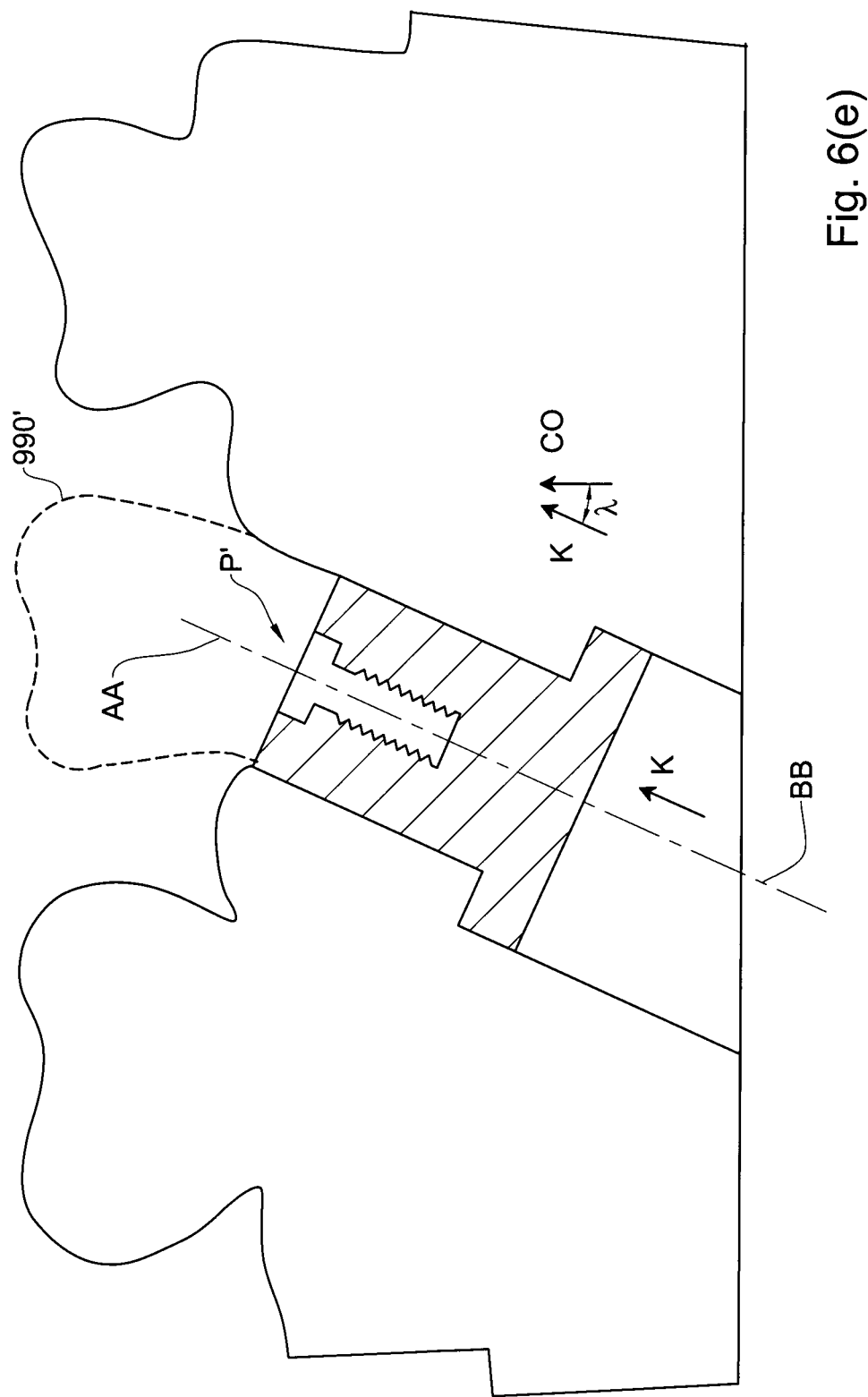
FIG. 6(e) illustrates in cross-sectional side view the dental analog example of FIG. 6(a) used in a variation of the example of a physical model of FIG. 5.
Figure 6F:
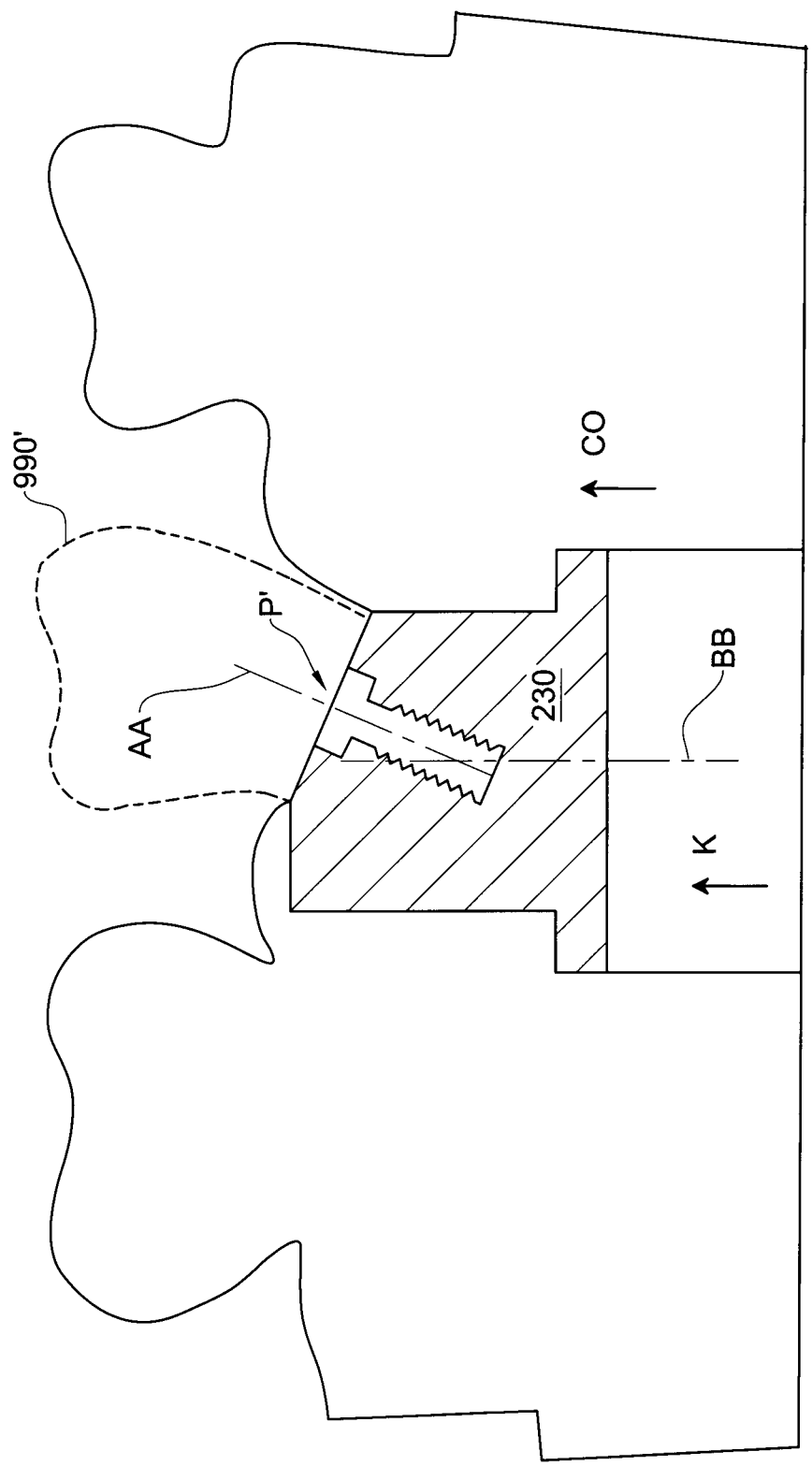
FIG. 6(f) illustrates in cross-sectional side view another variation of the dental analog example of FIG. 6(a) inserted into another variation of the example of the physical model of FIG. 5.

In another example, referring to FIG. 6(d), the analog flat portion 261 of the example of FIG. 6(a) can be omitted from the analog 230, and the enlarged apical portion 264 comprises instead a coronal face 265D that is not orthogonal to respective general coronal direction K, and thus also not orthogonal to longitudinal axis AA. Rather coronal face 265D is defined on a plane inclined to respective general coronal direction K, and thus also to longitudinal axis AA. Correspondingly, passageway 608 is formed with an inclined shoulder complementary to inclined coronal face 265D (rather than shoulder 657), which thus defines the longitudinal position of the implant 230 in the passageway 608 and the angular orientation of the implant with respect to the physical model 600 about respective general coronal direction K, and thus also about longitudinal axis AA.

As is also evident from the examples in FIGS. 6(a), 6(c) and 6(d), the relative longitudinal lengths between the coronal portion 262 and the apical portion 264 can be varied as desired, and the passageway 608 is corresponding formed to receive the implant in the general coronal direction K.

In another variation of the example of FIG. 6(a) the coronal portion 262 can be axisymmetrical about longitudinal axis AA, and instead the apical portion 264 is asymmetrical (the passageway 608 being complementarily shaped) to fix the angular disposition between the analog 230 and the physical model 600 about longitudinal axis AA.

In yet another variation of the example of FIG. 6(a), at least the coronal portion 262 can be externally threaded, and the passageway 608 can be complementarily internally threaded, to fix the angular disposition between the analog 230 and the physical model 600 about longitudinal axis AA.

In yet another variation of the example of FIG. 6(a), and referring to FIG. 6(g), the passageway 608 has a longitudinal axis BB that is angularly displaced with respect to the corresponding axis AA of the analog, which has an insertion reference axis parallel to longitudinal axis BB. Thus, the passageway in the physical model is complementarily shaped to the analog, and the respective insertion direction K is parallel to axis BB. In this example, while axis AA may be parallel or have an origination close to that of the coronal direction CO, the respective general coronal direction K can be significantly angularly displaced with respect to the coronal direction CO.

Figure 6H:
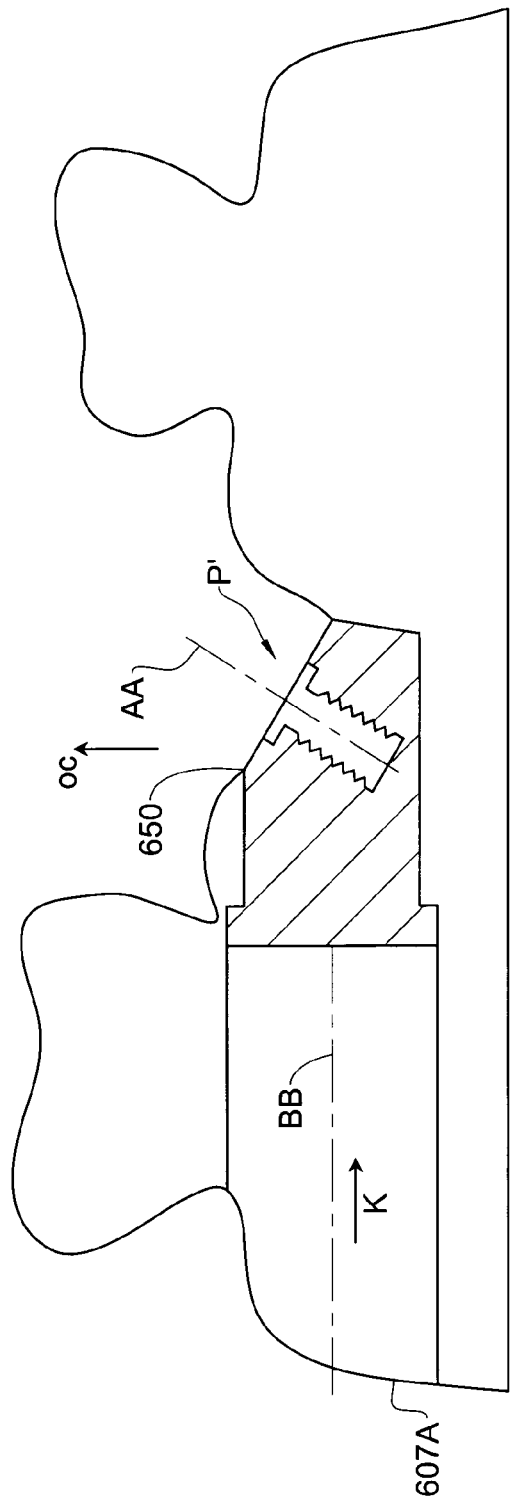
FIG. 6(h) illustrates in cross-sectional side view another variation of the dental analog example of FIG. 6(a) inserted into another variation of the example of the physical model of FIG. 5.

In yet another variation of the example of FIG. 6(a), and referring to FIG. 6(h), the passageway 608 has a longitudinal axis BB that is orthogonal or near orthogonal to the true occlusal direction OC, and has an analog insertion opening 607A on a side of the physical model 600 rather than on the base. The passageway in the physical model is complementarily shaped to the analog, and the respective insertion direction K is parallel to axis BB. In this example, the analog insertion opening 607A can be formed on parts of the physical model 600 representing some of the dental surfaces 115, but not any of the dental surfaces in the vicinity of and defining opening 650.

Figure 6I:
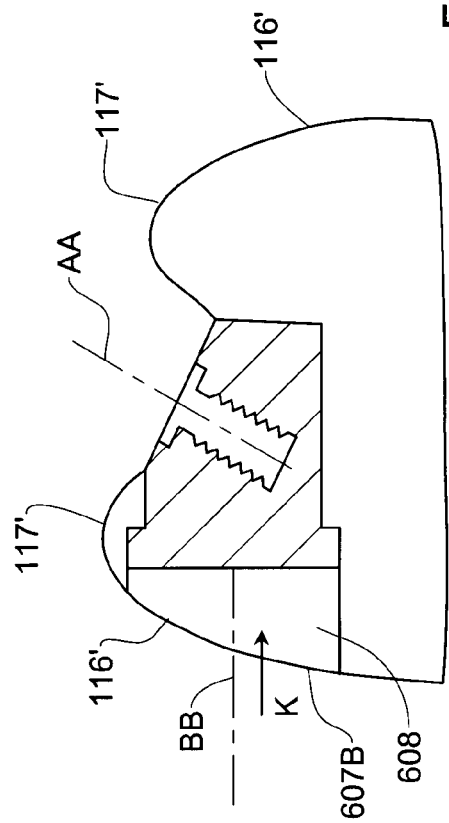
FIG. 6(i) illustrates in cross-sectional front view another variation of the dental analog example of FIG. 6(a) inserted into another variation of the example of the physical model of FIG. 5.

A variation of the example of FIG. 6(h) is illustrated in FIG. 6(i), which shows a cross-section of the respective physical model 600 along a coronal-buccal plane, and in which occlusal model surfaces 117' and side model surfaces 116' respectively represent occlusal facing dental surfaces and adjacent dental side surfaces of the dental surfaces 115 of the dental structure 100. In this example, the respective analog insertion opening 607B is wholly located on a side model surfaces 116' of the physical model 600, representing the gingival surfaces, for example, of the dental structure 100.

In yet other examples, the insertion path may include a change of direction. For example, referring to FIG. 5, another analog insertion opening (not shown) may be provided on the side of the physical model to enable the analog to be laterally inserted into passageway 608, for example in a buccal or lingual direction (i.e., into or out of the paper, for example), but at a position still axially displaced along axis BB from the implanted position, and then the analog is pushed along the axis BB to the implanted position.

Figure 7:
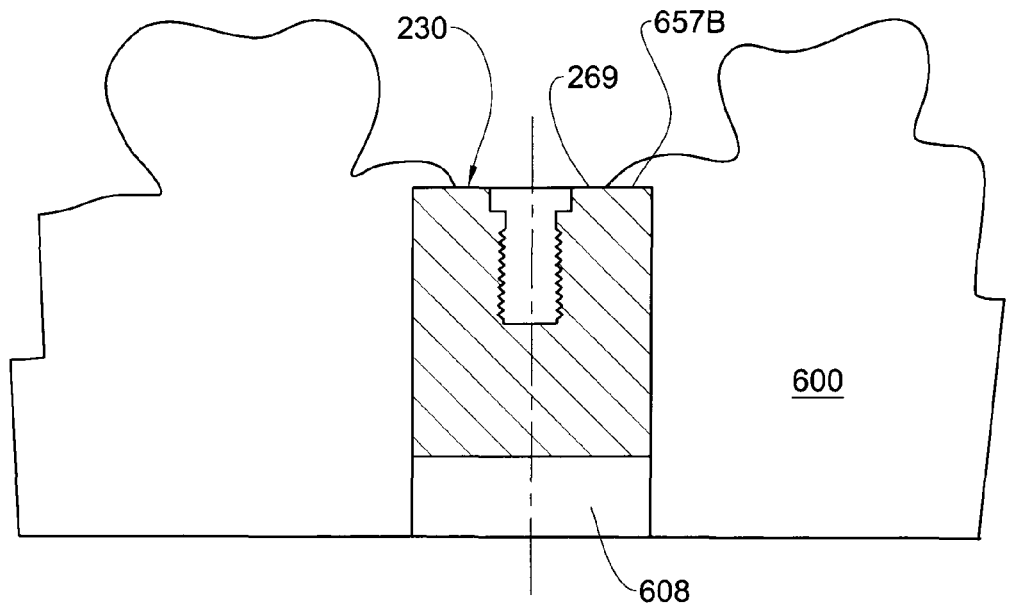
FIG. 7 illustrates in cross-sectional side view another example of a dental model corresponding to the dental structure of FIG. 1 and including a corresponding example of a dental analog inserted therein.

In yet another example, and referring to FIG. 7, the enlarged apical portion 264 of the example of FIG. 6(a) can be omitted from the analog 230, and, instead, coronal-facing face 269 abuts a shoulder 657B formed in passageway 608 complementary thereto, the shoulder 657B being coplanar with the installed position of the coronal-facing face 269. This arrangement limits the coronal translation of the implant 230 along passageway 608 to the installed position with respect to the physical model 600 in a manner similar to that provided by the coronal face 265 and the shoulder 657 of the example illustrated in FIGS. 5 and 6(a), mutatis mutandis. In this example, while the analog itself may be of uniform cross-section, it is evident that the exposed part of the coronal-facing face 269 has a maximum width dimension that is smaller than a maximum width dimension of another portion of the analog.

Figure 8:
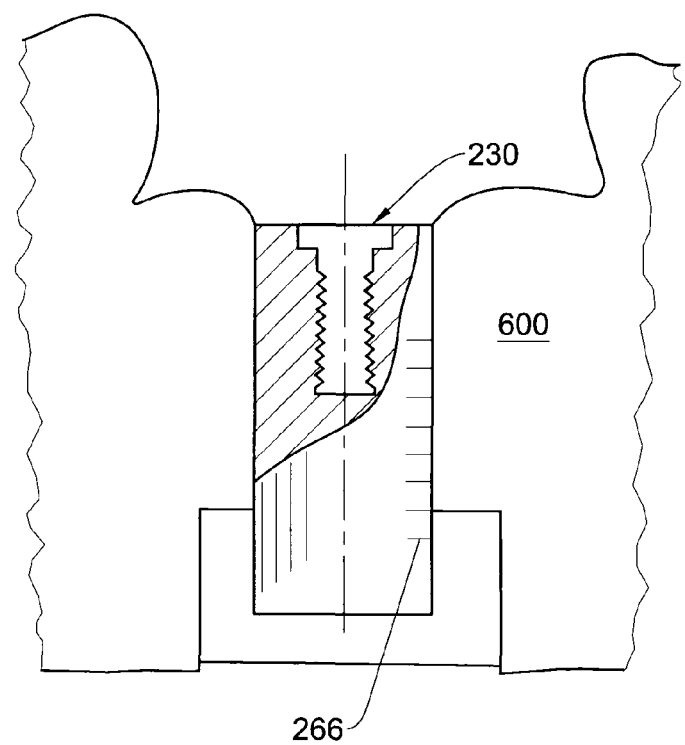
FIG. 8 illustrates in cross-sectional side view another example of a dental model corresponding to the dental structure of FIG. 1 and including a corresponding example of a dental analog inserted therein.
Figure 8A:
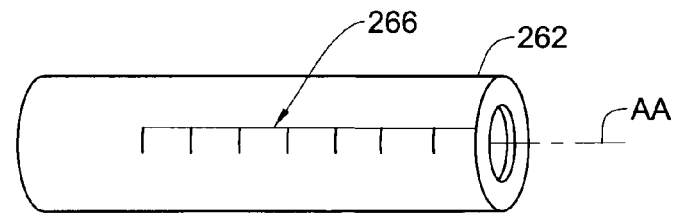
FIG. 8(a) illustrates in isometric view the dental analog example of FIG. 8.
Figure 8B:
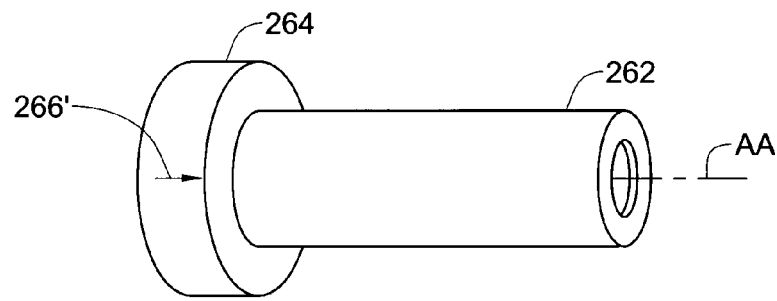
FIG. 8(b) illustrates in isometric view a variation of the dental analog example of FIG. 8(a).

In yet another example, and referring to FIGS. 8 and 8(a), the enlarged apical portion 264 of the example of FIG. 6(a)

can be omitted from the analog 230, and coronal portion 262 comprises visual markings 266 which are configured to facilitate longitudinal alignment of the analog 230 with the installation structure 690. For example, visual markings 266 can comprise a mark that can be manually aligned with shoulder 657 or any other suitable datum formed or marked in passageway 608. Alternatively, visual markings 266 can comprise a graduated scale provided along the side of the analog 230 that allows the depth of penetration of the analog 230 into the physical model 600 to be visually gauged. In use, the implant 230 can be inserted into passageway 608 until this alignment occurs, and the implant 230 is then cemented in place in its installed position with respect to the physical model 600.

In yet another example, and referring to FIG. 8(*b*), the analog 230 of the example of FIG. 6(*a*) can include the enlarged apical portion 264, but the analog is axisymmetric enabling free rotation within the passageway 608 about respective general coronal direction K, and thus also about axis AA. Apical portion 264 comprises visual markings 266' which are configured to facilitate rotational alignment of the analog 230 with respect to the installation structure 690 about respective general coronal direction K, and thus also about axis AA. For example, visual markings 266' can comprise a mark that can be manually aligned with a corresponding mark or other datum provided in the passageway 608, while the shoulder 657 acts as a mechanical stop. In use, the implant 230 can be inserted into passageway 608 until the enlarged apical end 264 is in abutment with shoulder 657, and then rotated therein about axis AA until this rotational alignment occurs, and the implant 230 can then be cemented in place in its installed position with respect to the physical model 600. Alternatively, the enlarged apical portion 264 of the example of FIG. 6(*a*) can be omitted from the analog 230, the visual markings 266' being provided, instead, on an apical end of the coronal portion 262, and in addition, visual markings 266 are also provided, in a similar manner to that of the example of FIGS. 8 and 8(*a*), mutatis mutandis, to also facilitate longitudinal alignment of the analog 230 with the installation structure 690. In use, the implant 230 can be inserted into passageway 608 and rotated therein until this longitudinal and rotational alignment occurs, and the implant 230 is then cemented in place in its installed position with respect to the physical model 600.

It is to be noted that in the above examples and in other examples of the analog 230 and of the corresponding physical model 600, the asymmetry of the coronal portion 262 may be achieved in a different manner to that illustrated with respect thereto to define the angular disposition P' of the analog 230 with respect to the passageway 608, and thus with respect to the physical model 600. For example, additional flat portions, similar to flat portion 261 but angularly displaced therefrom about longitudinal axis AA may be provided on the coronal portion 262. Alternatively, one or both of the coronal portion 262 and apical portion 264 can be formed having a non-axisymmetric cross-section, for example as a respective prismatic member having a polygonal cross-section (corresponding to a regular or irregular polygon), or having an oval cross-section, for example. In each case the passageway 608 is complementarily shaped to allow insertion of the analog in the general coronal direction to its installed position. Additionally or alternatively, a keyway may be formed in each one of the analog 230 and the passageway 608 of the physical model 600, and a corresponding key inserted when both keyways are aligned to fix the relative disposition between the analog 230 and physical model 600 in at least five degrees of freedom.

Figure 9:
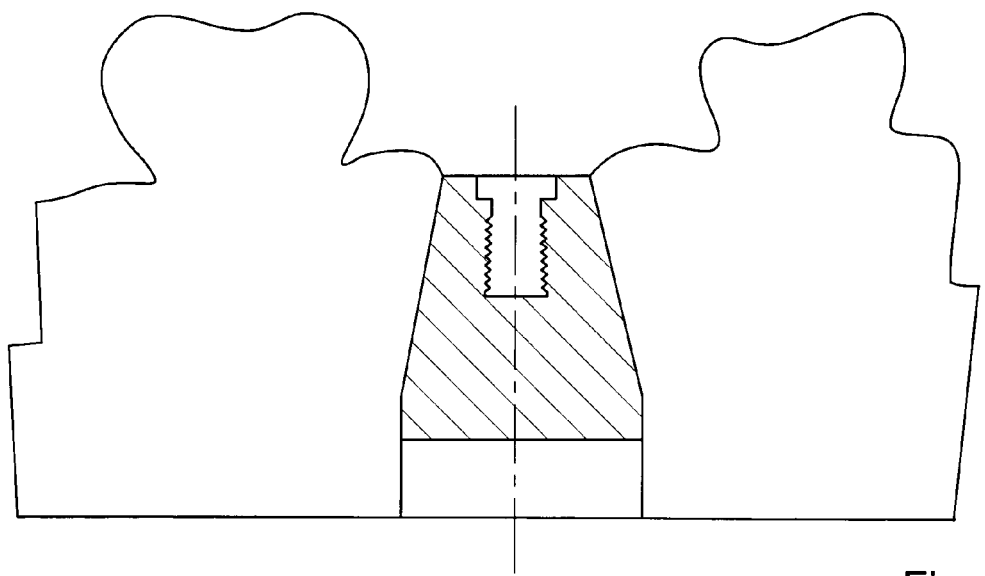
FIG. 9 illustrates in cross-sectional side view another example of a dental model corresponding to the dental structure of FIG. 1 and including a corresponding example of a dental analog inserted therein.

It is also to be noted that in the above examples and in other examples of the analog 230 and of the corresponding physical model 600, one or both of the coronal portion 262 and apical portion 264 are each formed having a generally uniform cross-sectional form along the longitudinal axis AA. Alternatively, and as illustrated in FIG. 9, in at least one variation of these examples or in at least another example, the coronal portion 262 may have a cross-section 262A that tapers in the general coronal direction, and the passageway 608 is complementarily tapered, to thereby define the longitudinal position of the implant 230 in the passageway 608 and thus with respect to the physical model 600; it is readily evident that additionally or alternatively, the apical portion 264 can be omitted, or the apical portion 264 can be formed with coronally tapering cross-section.

It is also to be noted that in at least some of the above examples and in other examples of the analog 230 and of the corresponding physical model 600, at least the exposed part of the respective coronal-facing face 269 (when the analog is in the respective installed position in the physical model 600) has a maximum width dimension that is smaller than a maximum width dimension of another portion of the analog. This ensures that these examples of the analog can be inserted into the physical model 600 in a direction that does not penetrate into the external surface 661, for example along a particular general coronal direction K, and at the same time limits penetration of the analog into the model to ensure that it is at the installed position at the end of penetration. The other portion of the analog having a greater maximum width than at least the exposed part of the respective coronal-facing face 269 can be at any desired location along the analog, for example at the opposed end thereof with respect to the coronal-facing face 269, or inbetween. It is readily evident that the maximum width differential can be achieved by providing this part with a larger cross-sectional shape or with a protrusion, as compared with the at least the exposed part of the respective coronal-facing face 269.

Figure 3:
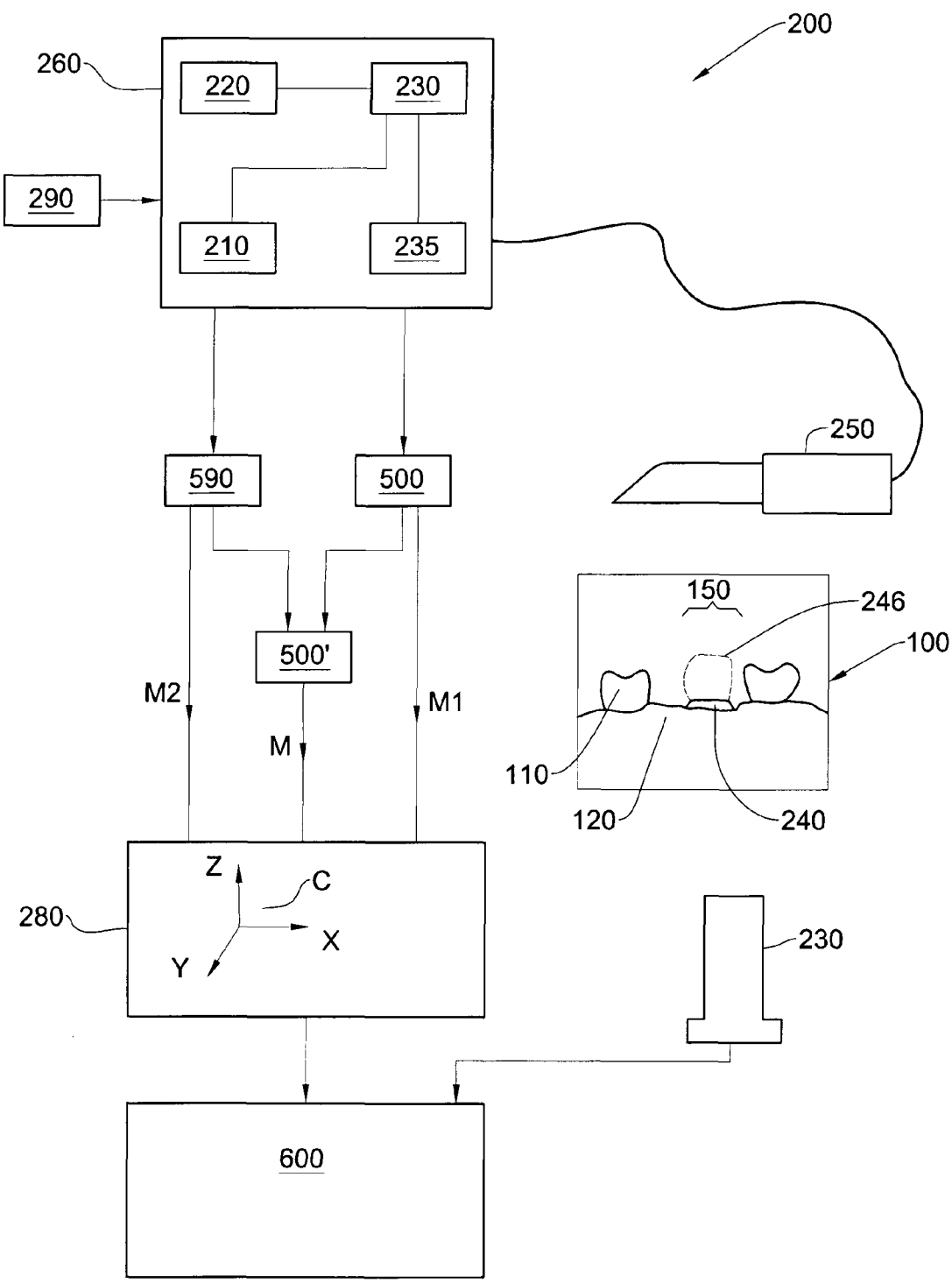
FIG. 3 is a schematic illustration of an example of a system according to a first aspect of the presently disclosed subject matter.

Referring to FIG. 3, an example of a system 200 for manufacturing a physical model, such as for example physical model 600, comprises a first subsystem 260 for generating a virtual (three-dimensional) model of the patient's dental structure 100 that includes the dental implant 240, operatively connected to a second subsystem 280 for manufacturing physical model 600 based on and corresponding to the virtual model, the physical model 600 being configured for enabling a physical analog 230 (corresponding to the dental implant 240) to be coupled, as already described in greater detail above.

The first subsystem 260 comprises a microprocessor or any other suitable computer system suitably programmed for operating on a virtual model of the aforesaid dental structure 100 to provide suitable manufacturing data to second subsystem 28, as will be disclosed in greater detail below with respect to the method 400. In this example, the computer system 260 comprises an input interface 210 such as a keyboard, mouse, tablet, and so on, an output device such as display 220, a processing unit 230, and a memory 235. Herein "display" refers to any device or system for delivering a presentation, which can include one or more of any information, data, images, sounds, etc, and thus the delivery can be in visual and/or audio form.

In this example, the subsystem 260 also comprises a scanner 250 that is configured for providing 3D surface data of surfaces, in particular of the dental structure 100 (or alternatively of an already existing physical model of the dental structure 100), including the hard dental surfaces 110 and soft dental surfaces 120 thereof, and also including the dental implant site 150. The scanner 250 is also configured for providing data relating to the spatial disposition P of the implant 240 with respect to the dental structure 100.

The scanner 250 is operatively connected to the computer system 260 and interacts therewith, and the subsystem 260 and/or the scanner 250 are suitably programmed for reconstructing such surfaces from the surface data provided, to provide a virtual model 500 of the dental structure 100. Suitable examples of such scanners are well known, and can include, for example, an intra-oral scanner marketed under the name of iTero (by Cadent Ltd., USA) which uses a hand held probe for determining three dimensional surface data based on confocal focusing of an array of light beams, and may optionally provide color data of the intraoral cavity in addition to the 3D surface data.

A scanning abutment 246 can be provided, which in use can be mounted to the dental implant 240 via the prosthesis interface part 248 and the prosthesis engaging part 241, and subsequently scanned directly or indirectly by the scanner 250. The scanning abutment 246 is characterized in having suitable 3D attributes, for example the scanning abutment 246 is shaped, and/or comprises suitable markers or other positional indicators on the visually exposed part thereof when mounted to the implanted implant 240, that provide information to enable the spatial disposition P of the dental implant 240 with respect to the dental structure 100 to be determined. In some cases, an impression abutment or a healing abutment can be used as a scanning abutment.

In alternative variations of this example of system 200, the scanner 250 can be omitted and the virtual model 500 can be provided to the subsystem 260 in any other suitable manner, for example via external virtual model source 290, which includes virtual model 500 having been generated in any suitable manner, including inter alia using suitable other scanning techniques, for example based on optical methods, direct contact methods, X-ray scanning, CT scanning, MRI scanning, ultrasound-based scanning, or any other type of scanning can be used, applied directly to the patient's dentition or to an impression or other negative model of the patient's dentition, or to an existing physical model thereof, as appropriate.

In any case, the subsystem 260 manipulates and operates on the virtual model 500 of the aforesaid dental structure 100 as disclosed below in the context of method 400 to generate manufacturing data for manufacturing the respective physical model 600, and this manufacturing data is provided to second subsystem 280.

The second subsystem 280 comprises a computer controlled manufacturing system configured for manufacturing the physical model 600 from the manufacturing data, which for example may be referenced to a machine coordinate system C. While in this example, the manufacturing process itself is a material removing process, such as CNC milling for example, in alternative variations of this example part or all of the manufacturing process can include a material additive process, for example a rapid prototyping process, for example using a 3D system stereo lithography machine, or can include any other suitable computer-controlled manufacturing process.

Referring to FIG. 4, an example of a method 400 for manufacturing a physical model, such as for example physical model 600, and which can be carried out using system 200, for example, broadly includes the following steps 420 and 450:

Step 420—receiving a virtual model of the physical dental structure and a virtual analog installation structure (also referred to herein interchangeably as a virtual analog socket structure) in association with said virtual model, said virtual analog installation structure being based on the dental analog;

Step 450 using said virtual model, manufacturing a physical model corresponding to said virtual model, the physical model being provided with an analog installation structure based on said virtual analog installation structure and thereby configured for enabling the dental analog to be inserted into said physical model through an analog insertion opening, wherein said analog insertion opening is spaced from a location in the physical model corresponding to the implant site in the physical dental structure.

Figure 4A:
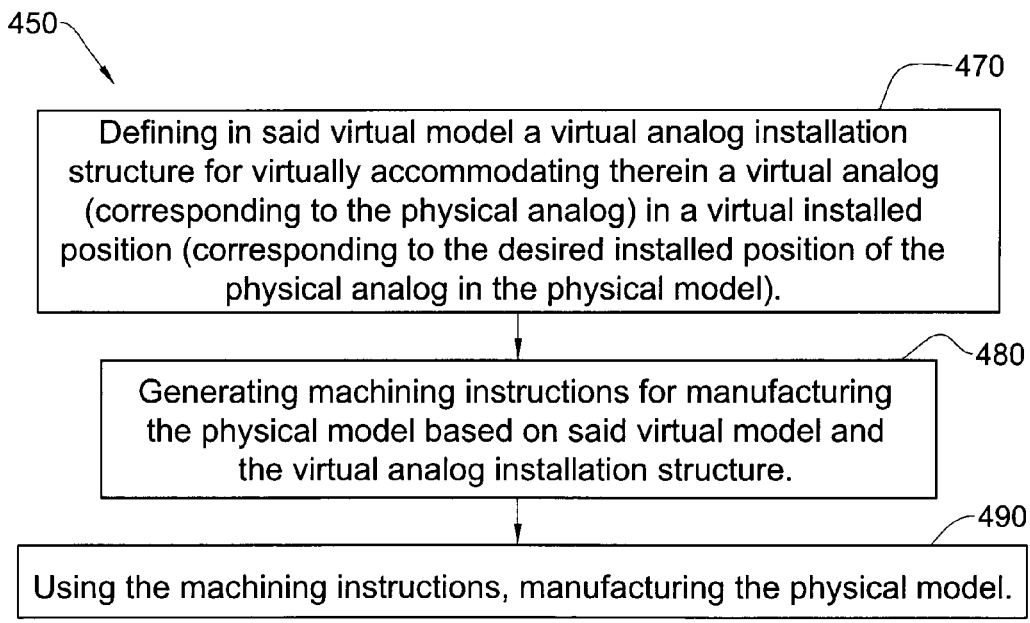
FIG. 4(a) is a schematic illustration of an example of step 450 of FIG. 4.
Figure 4B:
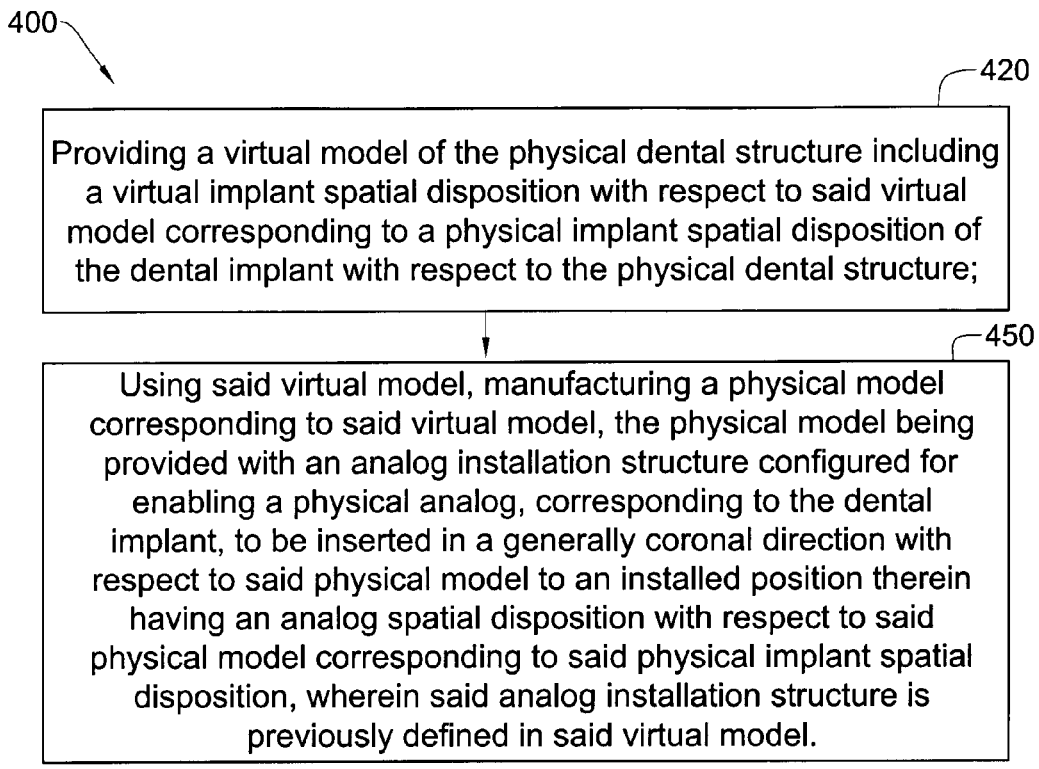
FIG. 4(b) is a schematic illustration of a variation of the example of FIG. 4.

In at least one variation of this example, and referring to FIG. 4(b), steps 420 and 450 can be as follows:

Step 420—providing a virtual model of the physical dental structure including a virtual implant spatial disposition with respect to said virtual model corresponding to a physical implant spatial disposition of the dental implant with respect to the physical dental structure;

Step 450—using said virtual model, manufacturing a physical model corresponding to said virtual model, the physical model being provided with an analog installation structure configured for enabling a physical analog, corresponding to the dental implant, to be inserted in a general coronal direction with respect to said physical model to an installed position therein having an analog spatial disposition with respect to said physical model corresponding to said physical implant spatial disposition, wherein said analog installation structure is previously defined in said virtual model.

In any case, the method 400 assumes that implant 240 has already been implanted in the dental structure 100 of the patient, and it is to be noted that implantation of implants in the intra oral cavity of patients is well known in the art. The method 400 also assumes that a particular type of analog 230 according to the first aspect of the presently disclosed subject matter, and corresponding to the dental implant 240, has been chosen, having a known or determinable external form 270.

Referring to each step in turn, step 420 comprises initially receiving, for example acquiring, an accurate three dimensional virtual model 500 of the dental structure 100, which as already stated includes the implant 240 and thus forms the focus of the particular implant procedure for a particular patient. Herein the term "virtual model" is synonymous with, and can be referred to interchangeably as, "three-dimensional model", "3D model", "virtual model", "3D representation", "3D digitized data", and the like. Referring also to FIG. 3, the virtual model 500 can be provided by scanning the intra-oral cavity dental structure directly in-vivo using the scanner 250 of system 200. Alternatively the virtual model 500 can be provided in any other any other suitable manner, for example via external virtual model source 290, i.e., including inter alia using suitable other scanning techniques, for example based on optical methods, direct contact methods, X-ray scanning, CT scanning, MRI scanning, ultrasound-based scanning, or any other type of scanning can be used, applied directly to the patient's dentition or indirectly thereto, for example applied instead to an existing physical model thereof, as appropriate.

The virtual model 500 includes, in addition to a virtual representation of dental surfaces 150 of the dental structure 100 (i.e., 3D information of the soft dental surfaces 120 and hard dental surfaces 110 at least in the vicinity of the implant zone 150), sufficient spatial (3D) data regarding the implanted implant 240 so that its spatial disposition P with respect to the dental structure 100, can be also be modeled with respect to the virtual model 500. The spatial disposition P of the implant 240 can be determined using at least two different scanning methods, to provide virtual implant spatial disposition data.

In a first scanning method, a first scanning procedure is applied directly to the dental structure 100 (the dental implant 240 being exposed to the intra-oral cavity) to enable creation of the virtual model 500 of the dental structure 100, to thereby provide an accurate virtual representation of dental surfaces 150 of the dental structure 100. Then, scanning abutment 246 is mounted to the dental implant 240 and a second scanning procedure is applied to the dental structure 100 with the scanning abutment 246 in situ, generating an auxiliary virtual model which includes a virtual portion thereof corresponding to the scanning abutment 246. Since the scanning abutment 246 has known 3D attributes, and the geometric relationship between the scanning abutment and the dental implant 240 is also fixed and known, analysis of this portion of the auxiliary virtual model provides information about the spatial disposition P of the dental implant 240 with respect to the dental structure 100, and thus enables this spatial disposition P to be modeled with respect to the first auxiliary virtual model to provide corresponding virtual spatial disposition data VP. Of course, the second scanning procedure can instead precede the first scanning procedure, in which case the scanning abutment 246 is removed from the dental implant 240 prior to proceeding with the first scanning procedure. In any case, a registration step can then be performed between the auxiliary virtual model and the virtual model 500, for example by matching corresponding virtual dental surfaces thereof, in particular by matching corresponding external hard virtual dental surfaces thereof, to provide the relative virtual disposition data VP of the implant with respect to the virtual model 500 from the virtual disposition already determined for the auxiliary virtual model.

Thus, the first scanning procedure provides the virtual representation of dental surfaces 150 of the dental structure 100 with unobscured surface details of the soft tissues in the vicinity of and around the periphery of the prosthesis engaging part 248, i.e., at interface 155, while the second scanning procedure provides the necessary information to determine the spatial disposition P of the implanted implant 240 with respect to the dental structure 100. This two-step scanning procedure can be of particular benefit when the details of the implant 240 are at least partially obscured by the soft tissues in the vicinity of the prosthesis engaging part 248, and/or where the scanning abutment 246 mechanically interferes with (for example presses against and deforms) the soft tissues in the vicinity of the prosthesis engaging part 248.

In a second scanning method, only a single scanning procedure is applied directly to the dental structure 100 (i.e., without any scanning abutment 246 being mounted thereto). In this scanning procedure at least a portion of the prosthesis engaging part 248 is exposed and captured during the scanning procedure, this portion being uniquely identifiable with respect to the dental implant 240. Analysis of a virtual portion of the virtual model 500 corresponding to the exposed prosthesis engaging part 248 enables this virtual portion to be matched to the geometry of the dental implant 240, which thus provides information about the spatial disposition P of the dental implant 240 with respect to the dental structure 100. In turn, this enables this spatial disposition P to be modeled with respect to the virtual model 500 to provide a corresponding virtual spatial disposition data VP of the virtual equivalent of the dental implant 240 with respect to the virtual model 500.

The virtual spatial disposition data VP thus includes dental implant data representing the location and orientation of the dental implant 240 with respect to the dental surfaces 115.

Alternatively, an indirect scanning technique can be used if a first prior physical model of the dental structure 100 (i.e., with the dental implant 240 already implanted in the dental structure 100) already exists, the aforementioned first scanning procedure of the first scanning method, or the second scanning method, may be applied to this first prior physical model rather than to the dental structure 100 i.e., instead of scanning the actual intraoral cavity of the patient. Furthermore, if there also exists a second prior physical model of the dental structure 100, obtained when the scanning abutment 246 was mounted thereto, the aforementioned first scanning procedure of the first scanning method may be applied to this second prior physical model rather than to the intraoral cavity of the patient. The first prior physical model can be provided, for example, in a conventional manner via a first physical impression of the dental structure 100, including the exposed implant 240 and subsequently casting the first physical impression with paste. The second prior physical model can be provided in a similar manner, for example via a second physical impression of the dental structure 100 taken with the scanning abutment 246 mounted to the implant 240 and subsequently casting the second impression with paste.

Thus, with respect to the virtual model 500, virtual spatial disposition data VP is determined, representative of the physical spatial disposition P of the dental implant 240 with respect to the dental structure 100.

For example, virtual spatial disposition data VP can be defined with respect to virtual model 500 in a similar manner to spatial disposition P or spatial disposition P', mutatis mutandis, i.e., can include the virtual spatial orientation of a virtual longitudinal axis VA, and the spatial position of a point VQ associated with a virtual analog 730 (corresponding to the physical analog 230), point VQ being at a fixed spatial relationship with respect to the axis VA.

Figure 10:
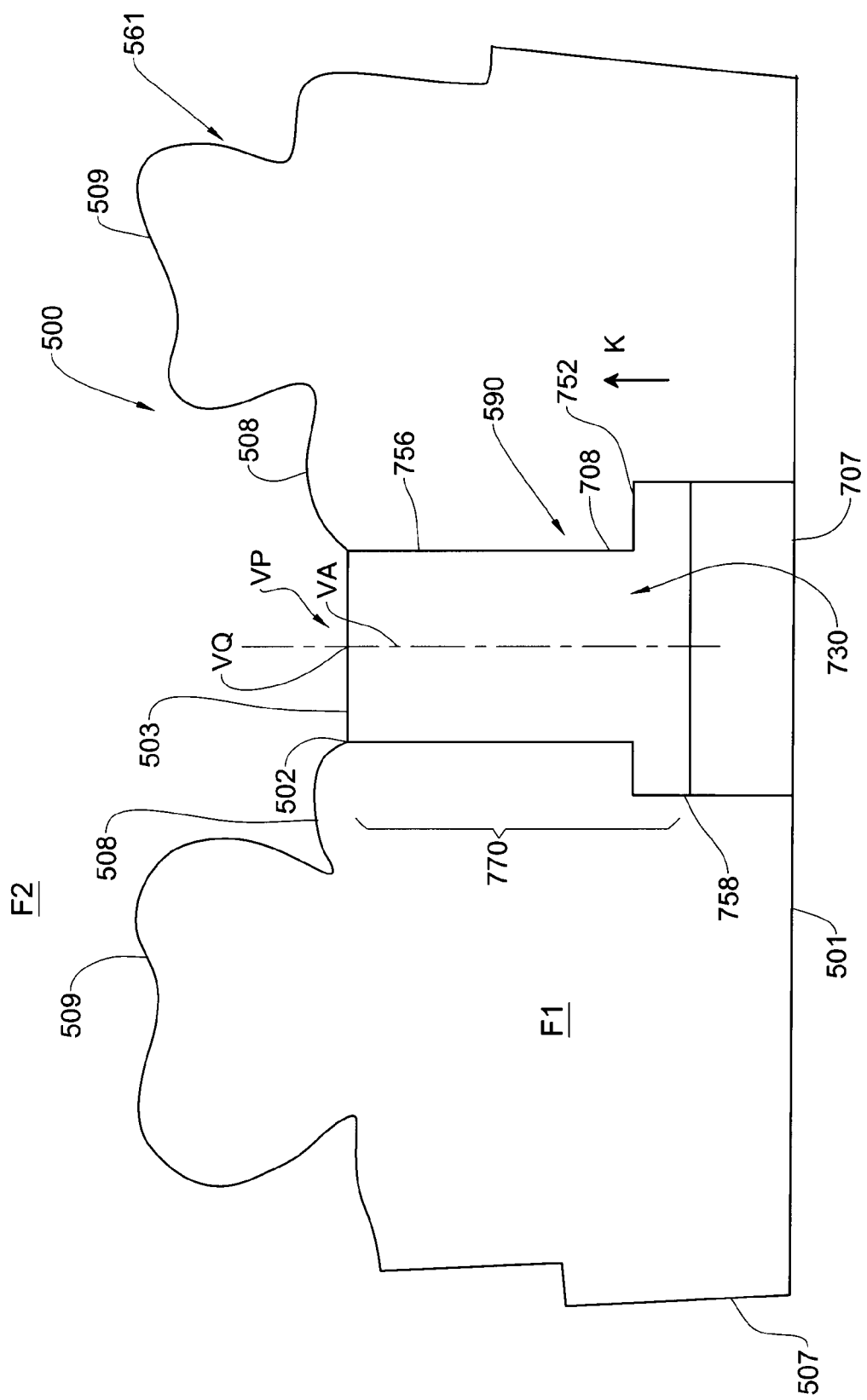
FIG. 10 illustrates in cross-sectional side view an example of a virtual model corresponding to the physical dental model of FIG. 5 and including a corresponding example of a virtual dental analog virtually inserted therein.

Referring to FIG. 10, virtual model 500 comprises a first external surface 561 virtually representative of dental surfaces 115 of said dental structure 100, including first virtual portions 509 corresponding to the hard dental surfaces 110, second virtual portions 508 corresponding to the soft dental surfaces 120, and a third virtual portion 502 corresponding to the interface 155 between exposed part of prosthesis engaging part 248 and soft dental surfaces 120.

Additionally, the virtual model 500 is operated on and modified to define a fully enclosed virtual volume corresponding to the enclosed volume of the respective physical model 600 that is to be manufactured. For example, and also referring again to FIG. 5, the virtual model 500 can be modified to include a virtual model base 506 corresponding to the desired physical model base 609, and comprising a respective external base surface 507 corresponding to the desired physical base surface 603. The virtual model base 506 can be generated in any number of ways. For example, a rectangular parallelepiped, or other prismatic shape or any other suitable shape, can be defined having a length and breadth greater, for example about 10% greater, than the overall length and breadth, respectively, of the first external surface 561, and a height for example about the same as the overall height of the first external surface 561. The base surface 507 thus generated is displaced in an apical direction A away from the first external surface 561, and the first external surface 561 is smoothly joined to the external base surface 507 in a virtual manner to create the enclosed virtual volume. The external base surface 507 is thus different from first external surface 561 and does not correspond to physiological surfaces, including dental surfaces, of said dental structure 100.

At least a part of the external base surface 507 is displaced from the aforesaid first external surface 561 in an apical direction A with respect thereto and away from the third virtual portion 502, and defines a virtual apical portion 501 corresponding to the desired physical apical portion 606 of the physical model 600.

Referring to FIG. 4(*a*), step 450 comprises a number of sub-steps, as follows:

Step 470—defining in said virtual model 500 a virtual analog socket structure (i.e., the virtual analog installation structure 590), for virtually accommodating therein a virtual analog (corresponding to the physical analog) in a virtual installed position (corresponding to the desired installed position of the physical analog in the physical model). In other words, the virtual analog installation structure 590 corresponds to the desired physical installation structure 690.

Step 480—generating machine instructions for manufacturing the physical model 600 based on said virtual model 500 and the virtual analog installation structure 590.

Step 490—using the machine instructions, manufacturing the physical model 600.

Herein, "virtual analog" is used interchangeably with "virtual analog structure".

Referring to step 470, this can include three sub-steps: step 470A, step 470B, and step 470C. In step 470A, and referring again to FIG. 10, the geometry of the appropriate virtual analog installation structure 590 corresponding to the desired physical installation structure 690, is provided, having corresponding 3D characteristics such as to ensure that virtual analog 730 can be virtually installed in the virtual analog installation structure 590 to a virtual installed position with respect thereto corresponding to the installed position of the dental analog 230 with respect to the corresponding physical installation structure 690, i.e. at virtual spatial disposition data VP, to define their relative positions in six degrees of freedom. The virtual analog installation structure 590 includes virtual passageway 708 having virtual internal walls 766 configured for allowing virtual insertion of the respective virtual implant 730 along the respective insertion direction to a virtual installed position, corresponding to the desired physical passageway 608 and internal walls 666, mutatis mutandis. Thus, and referring to the example of dental analog 230 and physical model 600 illustrated in FIG. 5 and FIG. 6(*a*), the virtual internal walls 766 define a virtual analog chamber 765, and passageway 708 comprises a first passageway portion 756, a shoulder 757, and a second passageway portion 758, corresponding to and having virtual 3D characteristics corresponding to the physical 3D characteristics required for the first passageway portion 656, shoulder 657, and second passageway portion 658. It is to be noted that at this point the second passageway portion 758 can have a different axial length than that of the eventual second passageway portion 658. These virtual components of passageway 708 are thus determined from the virtual external form 770 of the respective analog 730 is a manner similar to that described above for the passageway 608 of physical model 600 of FIG. 5 in the context of the external form 270 of the analog 230, mutatis mutandis.

Thus, the virtual analog installation structure 590 can be modeled for any type of implant 230, mutatis mutandis, having any external form 270, for example as illustrated in the figures, comprising a virtual passageway 708 having virtual internal walls 766 configured for allowing coronal insertion of the respective virtual implant 730 to a virtual installed position based on the external form 270 of the respective analog 230.

Thus, for example, it is possible for the first subsystem 260 to include in memory 235 (or in another memory operatively connected to the first subsystem 260) a library of virtual analog installation structures 590, each corresponding to one of a plurality of different types of dental analogs 230, in particular of the respective external forms 270 thereof, and the appropriate virtual analog installation structure 590 can be retrieved and operated on in steps 470B and step 470C below by identifying the corresponding virtual analog 770, which in turn corresponds to the actual dental analog 230 that has been chosen corresponding to the dental implant 240.

Alternatively, the appropriate virtual analog installation structure 590 can be imported to the first subsystem 260 from another external source.

In step 470B, the virtual analog installation structure 590 provided in step 470A is virtually aligned with respect to the virtual model 500 at virtual spatial disposition data VP to ensure that a virtual analog 730 can be virtually inserted to a virtual installed position therein corresponding to the installed position of the dental analog 230 in the physical model 600, the spatial disposition P', and which in turn corresponds to the spatial disposition P. This virtual alignment is relatively straightforward since the virtual spatial disposition of the virtual analog 730 with respect to the virtual analog installation structure 590 is fixed in six degrees of freedom at the virtual installed position, and since in the virtual installed position the virtual analog 730 will be at the already determined virtual disposition VP with respect to the first model 500. For example, the virtual analog 730 can be registered with respect to the virtual model 500 by aligning the virtual analog 730 at virtual spatial disposition data VP, and then registering the virtual analog installation structure 590 with the virtual analog 730, after which the virtual analog 730 can be removed.

In any case, the result is that the aligned virtual analog installation structure 590 is referenced to the same spatial/coordinate system as the virtual model 500.

Optionally, the aligned virtual analog installation structure 590 can be further modified, as necessary to ensure compatibility with the virtual model base 506, in particular to define virtual analog insertion opening 707 formed in virtual apical portion 706, corresponding to analog insertion opening 607 formed in apical portion 606. Thus, if necessary, the virtual passageway 758 can be extended in a general apical direction aligned with the virtual longitudinal axis VA, or shortened, to ensure such compatibility, and the virtual analog insertion opening 707 can be virtually defined as the intersection of virtual passageway 758 with virtual apical portion 706.

It is readily apparent that virtual analog insertion opening 707 is spaced from the parts of the virtual model corresponding to the implant site 150, in particular that virtual analog insertion opening 707 is spaced from virtual coronal opening 503. It is also readily apparent that virtual analog insertion opening 707 is different from virtual coronal opening 503.

In at least some examples the virtual analog insertion opening 707 is spaced from the outer model surface 661. In at least some examples the analog insertion opening 607 is at a location other than the first external surface 561. In at least some examples the virtual analog insertion opening 707 excludes a location in parts of the virtual model corresponding to the implant site 150.

Finally, a part of the virtual model 500 circumscribed by third virtual portion 502 is removed to provide virtual coronal opening 503, and the coronal end of the virtual analog installation structure 590 is virtually joined to the third virtual portion 502. The virtual analog installation structure 590 is thus open in a virtual sense at its coronal end via coronal opening 503, and at its apical end via virtual analog insertion opening 707.

In step 470C the virtual analog installation structure 590 can be virtually combined with the virtual model 500 to generate a modified virtual model 500'.

Figure 4C:
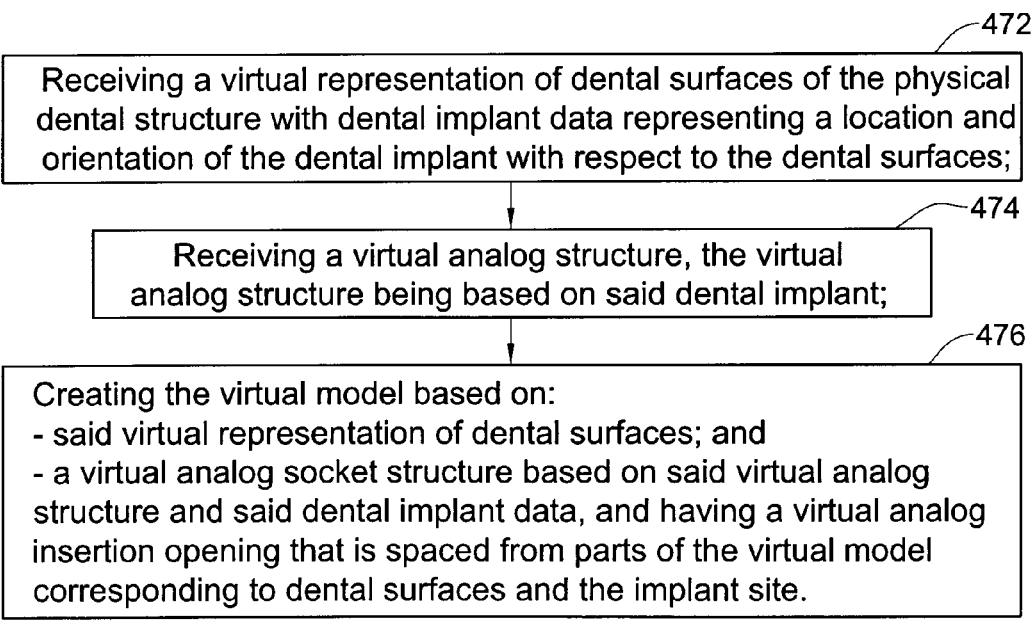
FIG. 4(c) is a schematic illustration of an example of a method for creating a virtual model according to a first aspect of the presently disclosed subject matter.

Referring to FIG. 4(c), it is thus readily apparent that the virtual model 500 can be created using a computer system, and implementing the following broad steps:

Step 472—receiving a virtual representation of dental surfaces of the physical dental structure with dental implant data representing a location and orientation of the dental implant with respect to the dental surfaces;

Step 474—receiving a virtual analog structure, the virtual analog structure being based on said dental implant; and Step 476—creating the virtual model based on:
  said virtual representation of dental surfaces; and
  a virtual analog socket structure based on said virtual analog structure and said dental implant data, and having an virtual analog insertion opening that is spaced from parts of the virtual model corresponding to dental surfaces and the implant site.

It is also readily apparent that the virtual analog socket structure, i.e., the virtual analog installation structure 590, is configured for virtually receiving therein the analog virtual model 730 via the virtual analog insertion opening 707 and along an insertion path, wherein the insertion path is along an insertion direction including at least one of:
  a general coronal direction K;
  a non-apical direction;
  a direction passing through the virtual representation of dental surfaces, i.e., first external surface 561, from a first location F1 with respect to the virtual model 500 corresponding to an inside D1 of the dental structure 100 to a second location F2 with respect to the virtual model 500 corresponding to an outside D2 of the dental structure (see FIG. 5 and FIG. 10).

Referring again to FIG. 4(a), in step 480 the modified virtual model 500' is suitably operated on to provide suitable machine instructions M to enable in step 490 computer controlled manufacture of the physical model 600 including the physical installation structure 690 corresponding to the virtual analog installation structure 590, for example using subsystem 280 (FIG. 3).

Alternatively, and referring again to FIG. 3, manufacturing step 490 has two stages. In this case, step 470C can optionally be omitted, and in step 480 the virtual model 500 is suitably operated on to provide a first set of machine instructions M1 for computer controlled manufacture of part of the physical model 600 excluding the physical installation structure 690. The virtual analog installation structure 590 is also suitably operated on to provide a second set of machine instructions M2 to finish the physical model 600 by the computer controlled manufacture of the physical installation structure 690 therein.

The exact nature of the machine instructions will depend, inter alia, on the type of computer controlled manufacture being used in step 490, for example CNC machining or rapid prototyping, and can be carried out using the second subsystem 280, for example.

A feature of CNC controlled manufacturing process of the model 600 according to this and at least some other examples of the presently disclosed subject matter is that the machine instructions for producing both, the external surface 661, base 609, chamber 665, passageway 608 and opening 607 of the model 600, are derived from the same virtual model 500 and are thus referenced to the same machine coordinate system C. This enables the same CNC controlled manufacturing system to be used for machining the external surface 661 and base 609 of the physical model 600, either in parallel or in series, with chamber 665, passageway 608 and opening 607 of the model 600, in an accurate and consistent manner, and in one machining operation or procedure. Further, there is no need for an intervening scanning operation or procedure to determine the 3D shape of the outer surface 661 or base 609, and then attempt to align the CNC machining of the cavity thereto, as can be required if the outer surface 661 on the one hand, and chamber 665, passageway 608 and opening 607 of the model 600, on the other hand, are manufactured using different methods or which are not based on the same virtual model. The manufacturing process according to at least this example can thus also be relatively quick and efficient.

The aforesaid computer controlled machining process can thus provide a high degree of dimensional accuracy at least in terms of the position and alignment of the chamber 665, passageway 608 and opening 607 of the model 600, with respect to the outer surfaces 661, and thus in terms of the position and alignment of analog 230 with respect to the model 600 when affixed therein, as the machining process for both the cavity 665 and chamber 665 on the one hand, and the passageway 608 and opening 607 of the model 600 on the other hand, are based on the same coordinate system.

In alternative variations of this example, the model 600, including the external surface 661, base 609, chamber 665, passageway 608 and opening 607 can be concurrently manufactured using any suitable manufacturing methods, for example rapid prototyping manufacturing methods.

In yet other alternative variations of this example, the model 600, including the external surface 661 and base 609 can be manufactured using a first manufacturing method, for example rapid prototyping manufacturing methods, while chamber 665, passageway 608 and opening 607 can be subsequently manufactured on this model using a second manufacturing method, for example CNC material removal manufacturing methods. Alternatively, model 600, can be produced using any other suitable computer-controlled manufacturing technique based on the virtual model 500.

The physical model 600, produced by CNC material removal methods and/or rapid prototyping methods, can be formed entirely of a hard material (or at least external surface 661 is formed entirely of a hard material), for example from a suitable hard machinable plastic or polymeric material or from hard materials commonly used in rapid prototyping manufacturing processes.

The physical model 600 can thus be made having uniform hardness. Alternatively the physical model can be formed as a composite physical model, for example as disclosed below regarding the second aspect of the presently disclosed subject matter for composite physical model 800, mutatis mutandis.

Once the physical model 600 with its respective installation structure 690 is completed, the analog 230 can be inserted into the physical model 600 in a general coronal direction K to the respective installed position, via apical base opening 607.

It is to be noted that the physical model 600 can optionally be formed with alignment features that allow the physical model 600 to be aligned with a physical model of the opposite jaw to provide proper occlusion, and the alignment features are first defined in a virtual manner in the virtual model 500, for example as disclosed in U.S. Pat. No. 7,220,124, US 2007/0077537 and US 2007/0154867, co-assigned to the present Assignee. Such a physical model 600 with alignment features can be provided according to the following method, for example:

(a) using a computer system:
   providing a three dimensional (3D) virtual dentition model of a patient's dentition including virtual model components corresponding to at least a part of each jaw thereof, and including the dental structure 100;
   providing 3D data representative of at least the spatial relationship between said jaws in occlusion;
   incorporating in said 3D virtual dentition model, one or more digitally created structural reference components defining an alignment arrangement for said 3D virtual dentition model based on said 3D data so as to define an updated 3D virtual dentition model, said one or more structural reference components configured to provide virtual occlusion alignment between said model components according to the spatial relationship; and (b) following step (a), preparing a physical three dimensional (3D) model including said physical model 600 and physical model components that respectively represent said virtual model components, based on said updated 3D virtual dentition model obtained in step (a), wherein said physical model components are produced incorporating one or more physical structural reference components respectively corresponding to one or more digitally created structural reference components to enable selectively providing physical occlusion alignment between said physical model components corresponding to said virtual occlusion alignment.

Alternatively, the physical model 600 can be configured for mounting onto any dental articulator.

According to the first aspect of the presently disclosed subject matter, a family of analogs may be conceived and provided, wherein each analog 230 of the family has the same external form 270, but wherein the analogs 230 in the family differ from one another in having a respective prosthesis interface analog part 238 and corresponding prosthesis engaging analog part 231 that is implant-specific, i.e., that correspond to the prosthesis interface implant part 248 and the prosthesis engaging implant part 241 of a specific type of dental implant, for compatibility with a particular type or make of prosthesis/permanent abutment configuration. For example, each of the analogs 230 in the family may correspond to a different one of a plurality of commercially available dental implants 240. This allows the method 400 to be effectively applied to a wide range of cases where the dental implant 240 can be chosen for compatibility with any one of a range of such prosthesis/permanent abutment configuration, while the external form 270 of the analog 230 is effectively standardised, enabling the form of the opening 607, passageway 608 and chamber 665 formed in the physical model 600 can be standardized, and likewise the virtual equivalents of these components can also be standardized.

In another example according to the first aspect of the presently disclosed subject matter, a particular desired analog is not originally suitable for, or is unable to be, press-fitted into a complementarily-shaped chamber, formed in the physical model, in a general coronal direction. For example, and referring to FIG. 11, the desired analog 230' can be a commercially available analog that can comprise laterally projecting protrusions designed for anchoring the analog in a plaster model when the model is cast using prior art methods, in which the analog is first aligned in the mold prior to casting. The system and method according to the first aspect of the presently disclosed subject matter can be applied in at least two different ways, for example as follows.

Figure 11:
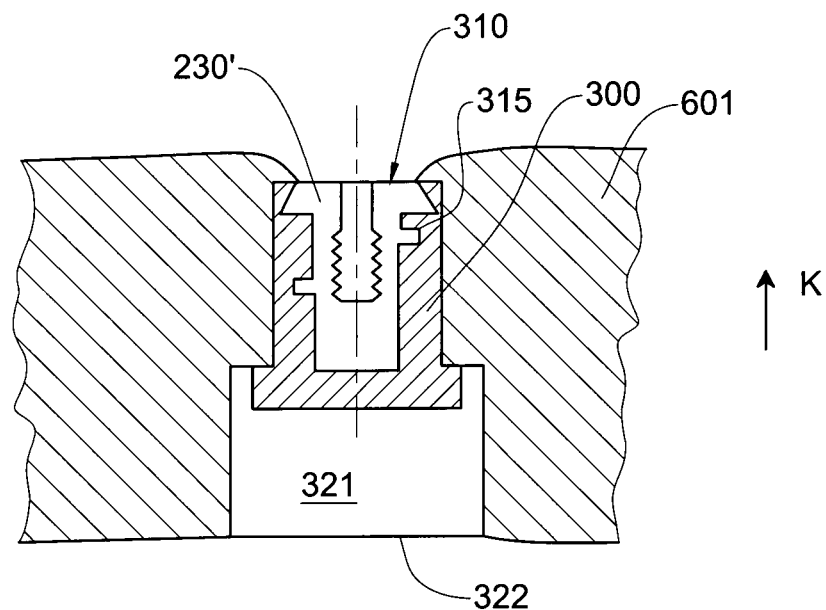
FIG. 11 illustrates in cross-sectional side view another example of a dental model corresponding to the dental structure of FIG. 1 and including a corresponding example of a dental analog inserted therein.

In a first such application of system and method according to the first aspect of the presently disclosed subject matter, and referring to FIG. 11, the physical analog 230' is embedded in a jacket 300 to form a composite analog 310. For example, the jacket 300 is made from a machinable material, which is milled or otherwise machined in situ on the analog 230' to have a relative smooth external shape 315 that is readily insertable in the general coronal direction K, into the in the physical model, referred to herein by the reference numeral 601, and which enables the composite analog 310 to be fixed therein in six degrees of freedom at spatial disposition P'. Thus, the external shape 315 can correspond to or be similar to the external form 270 as described above to any one of the examples of analog 230, for example. On the other hand, the physical model 601 has a respective analog physical installation structure 690, for example including passageway 321 and chamber 320, and model base opening 322.

The shape and relative position of the outer surface 315 of the jacket 300 that is to mate against the internal surface 325 of chamber 320 can be predefined, for example. The shape and relative position of the outer surface 315 of the jacket 300 that is to mate against the internal surface 325 of chamber 320 can be predefined. The jacket 300 is formed on the analog 230'—for example the analog 230' is cast or otherwise embedded in a blank of material, and the jacket 300 is machined until a desired form is provided for outer surface 315. Alternatively, a cast material can be poured into a precision mold of a predefined internal shape, while analog 230' is being held in a predefined spatial relationship with respect thereto by an accessory such as a suitable jig or the like.

The method steps as disclosed above and with reference to FIG. 4 are applicable to this example of physical model 601, mutatis mutandis, with the main difference that in general at least some of the steps therein relating to the analog 230, chamber 665, passageway 608 and opening 607, and their virtual equivalents, can be applied, in this example, to the composite analog 310, respective chamber 320, respective passageway 321 and respective opening 322 instead, mutatis mutandis, while step 420 for the second example is substantially the same as for the first example relating to physical model 600 mutatis mutandis.

In step 470, though, the virtual analog 730, while now representative of the physical analog 230' rather than analog 230, is further representative of the jacket 300, and thus in particular corresponds to the composite analog 310. In any case, in step 470, the resulting composite analog 310 can be scanned, for example, to generate the corresponding virtual analog 730.

In step 450, the outer surface and the chamber 320 of the physical model 601 are manufactured in a similar manner to that for physical model 600, mutatis mutandis, and the composite analog 310 can then be installed into the chamber 320 via opening 322 and passageway 321 in a general coronal direction K such that the analog 230' is aligned with the model 601 in spatial disposition P'. The physical model 601 can be made having uniform hardness, for example as disclosed herein for physical model 600, mutatis mutandis, or can be formed as a composite physical model, for example as disclosed below for composite physical model 800, mutatis mutandis. In any case, once the physical model has been manufactured, the composite analog 310 is inserted into chamber 320 via opening 322 and passageway 321.

Figure 12:
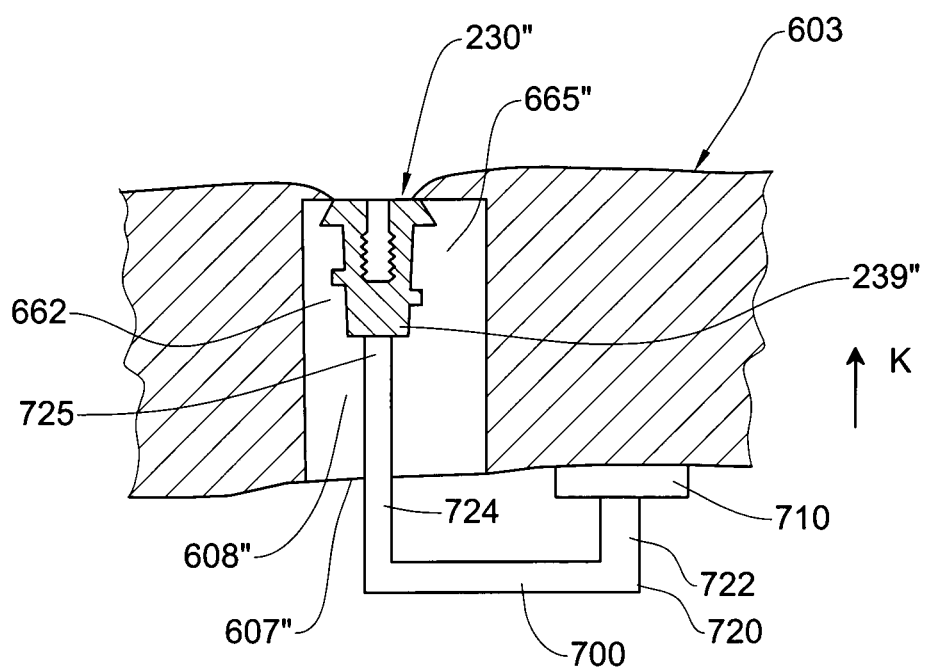
FIG. 12 illustrates in cross-sectional side view another example of a dental model corresponding to the dental structure of FIG. 1 and including a corresponding example of a dental analog inserted therein using a jig.

Alternatively, and in a second such application of system and method according to the first aspect of the presently disclosed subject matter, a physical model of the dental structure 100 is provided in a similar manner to that disclosed herein for the above examples, mutatis mutandis, with some differences. Referring to FIG. 12, the first difference is that the respective chamber 665" and respective passageway 608" are provided being significantly larger (i.e., having larger cross-section) than required for accommodating the analog 230' in a tight fit configuration, and the respective chamber 665" and respective passageway 608" can be of any desired shape so long as the analog 230' can be inserted therein in a general coronal direction, with a lateral clearance 662 therebetween, to the installed position at spatial disposition P'. In this case, the virtual analog installation structure is generated to provide a corresponding clearance for the virtual analog corresponding to the analog 230'. Once the physical model 603 is manufactured, an accessory in the form of an accessory in the form jig 700 is used for holding the analog 230' within the chamber 665", via opening 607" and passageway 608" in the desired position and orientation therein, i.e., in spatial disposition P' having been inserted therein in a general coronal direction K. A filling and fixing material, for example epoxy resin, is then introduced in the clearance gap 662 and allowed to set, cementing the analog 230' in place, after which the jig 700 can be disengaged from the analog 230' and from the model 603.

The jig 700, according to a first example thereof, comprises a base 710, and a substantially rigid, inverted U-shaped strut 720, having one arm 722 rigidly attached to the base 710 and a second arm 724 having a free end 725 onto which an analog 230' can be mounted at apical end thereof 239" (opposed to the abutment receiving end thereof) in a known and unique spatial relationship with respect thereto. There is thus a unique and fixed spatial relationship between the end 725 and the base 710. The shape of the jig is only illustrative, and any suitable arrangement can be used that has a fixed geometrical relationship between the model-engaging base and the analog apical end. Furthermore, the mating platform 670 is attached to the model base, in a unique mating spatial position (or indeed to another structure in a known fixed relationship to the model 603) remote from parts of the model 603 representing dental surfaces, and thus facilitates the cementing procedure for the user as there is a minimum or zero obfuscation of the chamber 665" and analog 230' by the jig.

The physical model 603 according to this example can be made having uniform hardness, for example as disclosed herein for physical model 600, mutatis mutandis, or can be formed as a composite physical model, for example as disclosed below for composite physical model 800, mutatis mutandis.

It is to be noted that the first subsystem 260 in which virtual models are created and operated on according to any of the examples of the presently disclosed subject matter does not necessarily need to be located in the same geographical location as the scanner 250 and patient. Thus, while the scanning of the patient is usually done at a dental clinic by the dentist or other dental practitioner, the dental clinic can instead or additionally be linked to one or more dental labs, and possibly also to a dental service center via a communication system or network such as for example the Internet or other suitable communications medium such as an intranet, local access network, public switched telephone network, cable network, satellite communication system, and the like. Additionally or alternatively, the communication system can include postal or courier services, the data being communicated via a transportable medium such as an optical disc, magnetic disc and so on. In any case, once the virtual model is created, the physical dental model, and other dental procedures not carried out on the actual patient, can be carried out by the dental lab which receives the required data generated by the method 400 via the communications system. Additionally or alternatively, the physical dental model can be manufactured in one location, and sent to another location in which the analog is implanted in the physical dental model.

Figure 13:
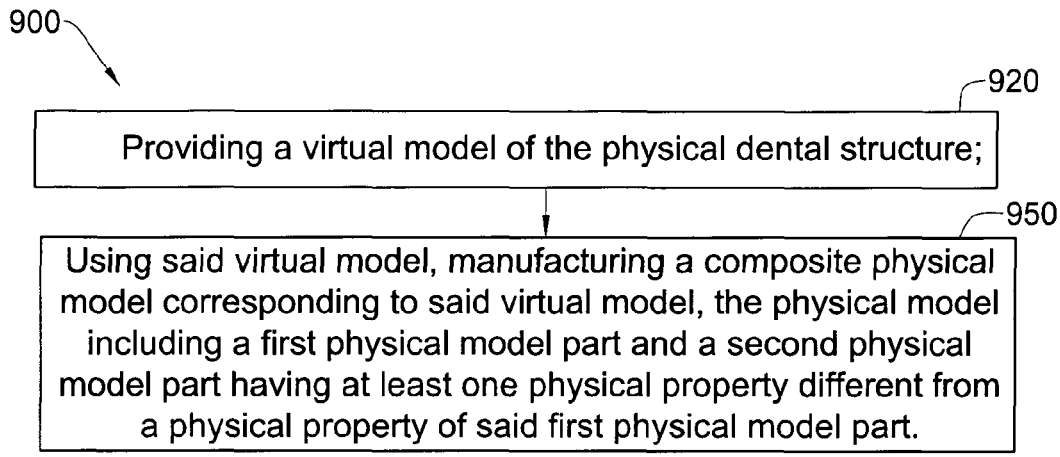
FIG. 13 is a schematic illustration of an example of a method according to a second aspect of the presently disclosed subject matter.
Figure 13A:
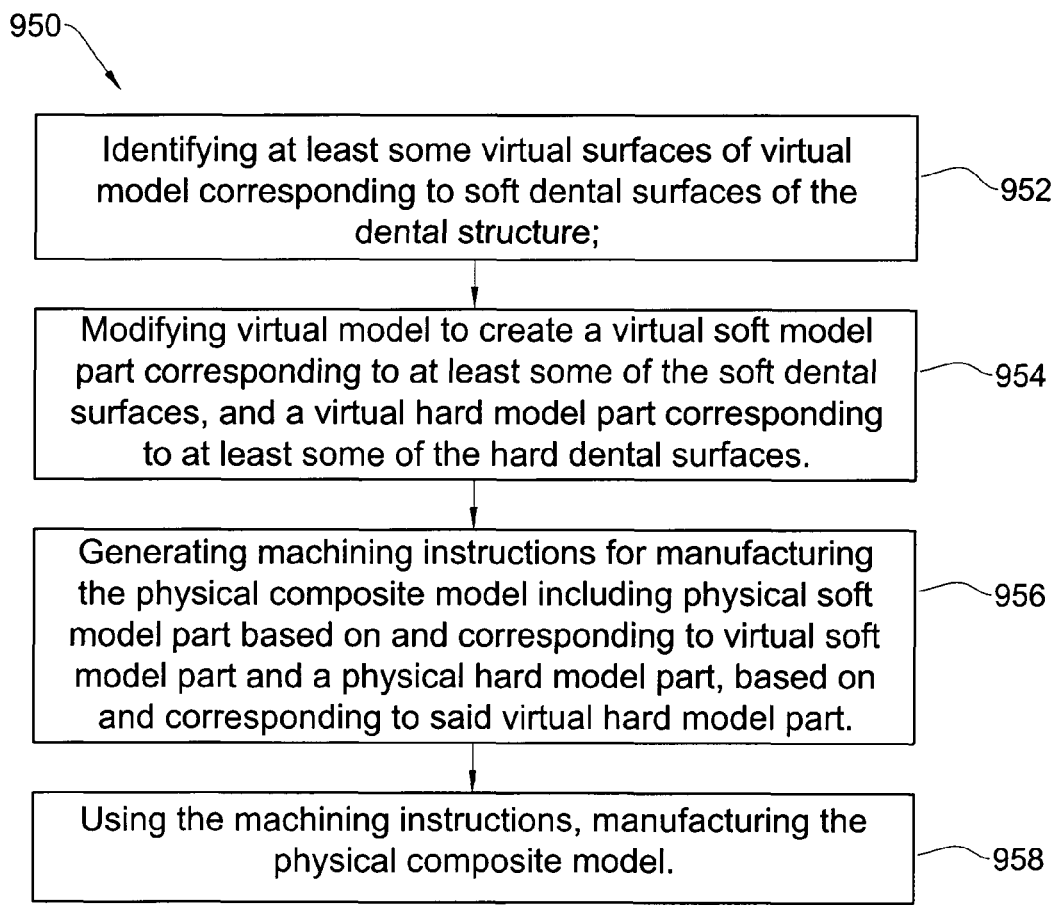
FIG. 13(a) is a schematic illustration of an example of step 950 of FIG. 11.

Referring to FIG. 13, an example of method 900 for providing a composite physical model of a dental structure according to the second aspect of the presently disclosed subject matter broadly includes the following steps 920 and 950:

Step 920—providing a virtual model of the physical dental structure;

Step 950—using said virtual model, manufacturing a composite physical model corresponding to said virtual model, the physical model including a first physical model part and a second physical model part having at least one physical property different from a physical property of said first physical model part.

In the following example, the dental structure is the aforesaid dental structure 100 which includes a dental implant 240 implanted therein at a particular implant site 150, and includes hard dental surfaces 110 and soft dental surfaces 120 thereof. Thus step 920 can correspond to step 420 according to the first aspect of the presently disclosed subject matter, mutatis mutandis, wherein virtual model 500 of the dental structure 100 is generated. However, it is to be noted that method 900 is not limited to such a dental structure, and can thus also be applicable be applicable for the manufacture of other dental physical composite models in a similar manner to that disclosed herein, mutatis mutandis, whether configured for having an analog installed therein in any suitable manner, or whether the physical composite model is not configured for incorporating an analog—for example a regular dental model, or one used for manufacturing and fitting a prosthesis on a preparation.

In other words, the method 900 is also applicable, mutatis mutandis, to other dental structures having hard dental structures (for example optionally including a tooth preparation) and soft dental structures, and optionally having an absence of any implants in the dental structure. For example, where the dental structure lacks a dental implant, step 920 can be similar to step 420, but can exclude any activity directed to determining the spatial disposition of the implant, mutatis mutandis, and similarly step 950 excludes manufacturing an analog installation structure, mutatis mutandis.

Figure 14A:
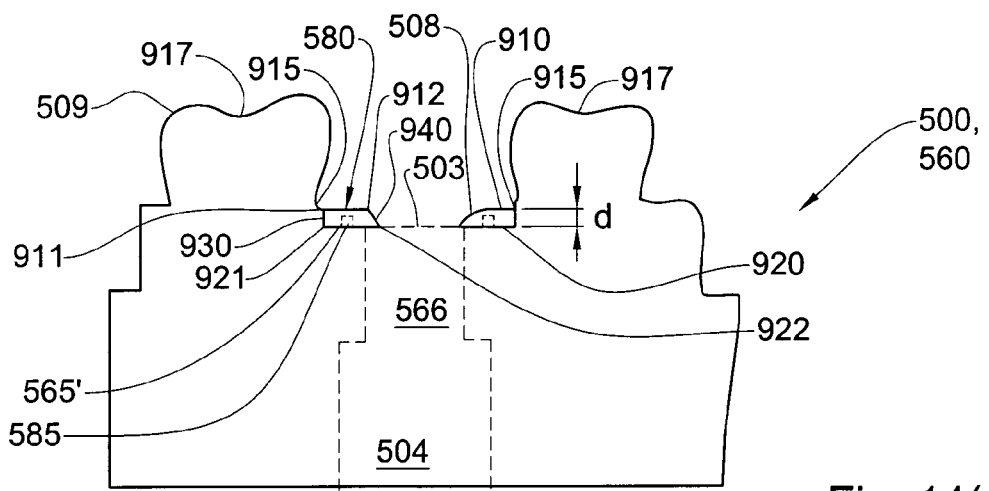
FIGS. 14(a) to 14(c) illustrate in side view a number of stages associated with providing a composite physical model example according to the second aspect of the presently disclosed subject matter.
Figure 14B:
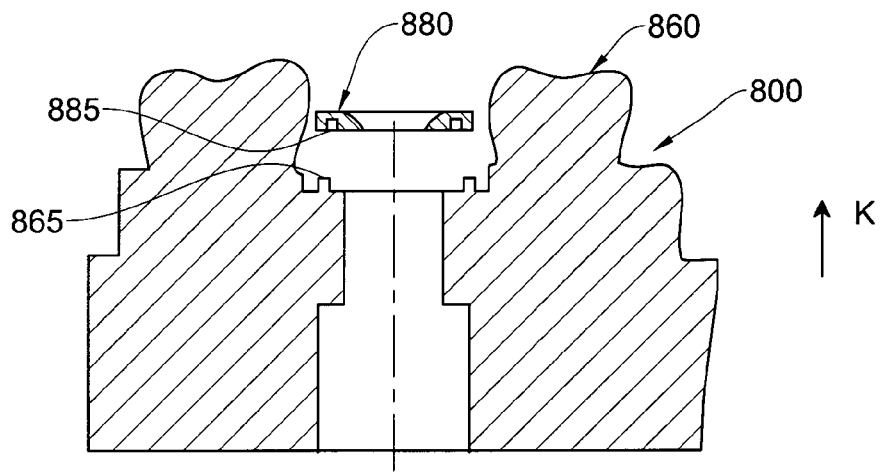

Referring to FIG. 13(*a*), and to FIGS. 14(*a*) to 14(*c*), step 950 can include the following substeps:

Step 952—identifying at least some virtual surfaces of virtual model 500 corresponding to some or all of the soft dental surfaces 120 of the dental structure 100;

Step 954—modifying virtual model 500 to create a virtual soft model part 580 corresponding to at least some of the soft dental surfaces 120, and a virtual hard model part 560 corresponding to at least some of the hard dental surfaces 110.

In step 952, a zone or surface 910 is defined on the second virtual portions 508, around the virtual coronal opening 503 corresponding to the zone of soft dental surfaces 120 of the original dental structure 100 that surrounds the implant site 150 and that is to be represented in the composite model 800 by the soft model part. For example, surface 910 can extend up to the virtual gingival margins 915 of the virtual teeth 917 (of the virtual portions 509) that are adjacent the virtual coronal opening 503.

The particular second virtual portions 508 can be identified by, and surface 910 can be defined by, the user, in an interactive manner using the first subsystem 260 of system 200 (FIG. 3), for example. Alternatively, second virtual portions 508 can be identified and/or surface 910 can be defined in an automated or semi-automated manner. For example, the computer system 260 can be programmed to automatically identify the virtual coronal opening 503 and then identify and define surface 910 by radiating outwardly along the second virtual portions 508 of the virtual model 500 by a fixed spacing, for example, or until the curvature of the virtual model 500 indicates that the surface is curving in an upward direction, which is indicative of the first virtual portions 509.

It is evident that for at least this particular application of method 900, it is only desired for a relatively small area around the implant site 150 to be reproduced in the composite model 800 using a relatively soft material, while the remainder of the composite model 800, including other parts thereof that correspond to other soft dental surfaces 120, may be included in the hard model part. In other applications of method 900, other parts or all of the parts of the virtual model 500 that represent the soft dental surfaces 120 may be included in the soft model part.

In step 954, once surface 910 is defined, a second virtual surface 920 is defined, for example by displacing a copy of surface 910 in an inwardly or apical direction by a predefined displacement "d". For example, displacement "d" can correspond to spacing between the most coronal part of surface 910 and the position of third virtual portion 502 (corresponding to the position of the exposed part of prosthesis engaging part 248), or may be some percentage greater than this spacing, for example 105%, 110%, 125%, 150% or 200% or more of this spacing. Then, an additional outer lateral virtual surface 930 is defined, joining together the outer edges 911 and 921 of surfaces 910 and 920, respectively, and where necessary an additional inner lateral virtual surface 940 is defined, joining together the inner edges 912 and 922 of surfaces 910 and 920, respectively.

Alternatively, second surface 920 can be defined in any other suitable manner—for example by defining a plane (or any other surface, e.g. a part-cylindrical surface) at a desired orientation (for example parallel to the occlusal plane or to any other suitable reference plane), displacing this plane in an apical direction AP from the position of portion 502 by a suitable displacement or maintaining the plane at portion 502, and then intersecting the plane with second virtual portions 508, for example.

The virtual hard model part 560 is then created by removing surface 910 and inner lateral virtual surface 940 from the virtual model 500, and adding surface 920 and outer lateral virtual surface 930. The virtual hard model part 560 corresponds to the hard model part 860 of the composite physical model 800 that is to be manufactured.

A virtual soft model part 580, separate from the virtual hard model part 560, is also created by joining surface 910 and inner lateral virtual surface 940 to surface 920 and outer lateral virtual surface 930, and the virtual soft model part 580 corresponds to the soft model part 880 of the physical composite model 800. In at least some variations of this example, a small spacing may be desired between the soft model part 880 and the hard model part 860, for example for introducing an adhesive therebetween, and in such cases the virtual soft model part 580 or the virtual hard model part 560 is correspondingly modified by displacement of the corresponding surface 920 thereof.

Referring again to FIG. 13(*a*), step 950 can further include the following substeps:

Step 956—generating machine instructions for manufacturing the physical composite model 800 including physical soft model part 880 based on and corresponding to virtual soft model part 580 and a physical hard model part 860, based on and corresponding to said virtual hard model part 560.

Step 958—using the machine instructions, manufacturing the physical composite model 800.

In step 956 the virtual soft model part 580 and the virtual hard model part 560 (which optionally may be combined in to a single virtual model while retaining their characteristics) are suitably operated on, for example via subsystem 260, to provide suitable machine instructions to enable in step 958 computer controlled manufacture of the physical composite model 800 (which in this particular application of method 900 also includes the physical installation structure 690 corresponding to the virtual analog installation structure 590), for example using subsystem 280 (FIG. 3).

The exact nature of the machine instructions will depend, inter alia, on the type of computer controlled manufacture being used in step 958, for example CNC machining or any type of rapid prototyping (for example stereo lithography, printing, sintering, etc.), and can be carried out using the second subsystem 280, for example.

In the example illustrated in FIGS. 14(*b*) and 14(*c*), the hard model part 860 and the soft model part 880 are separately manufactured and then coupled together. The hard model part 860 can be manufactured based on and corresponding to the virtual hard model part 560, in a similar manner to that disclosed above for the manufacture of physical model 600 based on virtual model 500, mutatis mutandis. Thus, for example, a CNC material removal operation or procedure can be conducted on a suitable hard material blank, or a suitable rapid prototyping method can be used, or a combination of both, or any other suitable computer-controlled manufacturing technique based on the virtual hard model part 560.

The soft model part 880 can be formed from suitable relatively soft material and can be manufactured based on and corresponding to the virtual soft model part 580 using the corresponding machine instructions, in a similar manner to that disclosed above for the manufacture of physical model 600 based on virtual model 500, mutatis mutandis. Preferably, the soft material is similar in at least one of texture, resilience, color and softness to the natural gums, but other materials which are non-rigid can also be suitable, or that are at least softer than the material of the hard model part, and/or have different colors to the natural gums. For example, the soft material can be rubber, silicone, or any other soft tissue material used in the art to create composite dental models.

The soft model part 880 can be formed in a number of different ways, based on the virtual hard model part 560 and using the appropriate machine instructions derived therefrom. For example, soft model part 880 can be formed via a rapid prototyping manufacturing method, using a suitably soft material—for example using an Objet rapid prototyping machine (for example as disclosed in website objet.com), and a suitable material, for example as marketed under "TANGO", which can be selectively provided with different levels of rigidity. Alternatively, and depending on the actual hardness of the soft model part, a CNC material removal operation or procedure can be conducted on a suitable soft material blank, or any other suitable computer-controlled manufacturing technique based on the virtual hard model part 560 and using the appropriate machine instructions derived therefrom.

Alternatively, a mold can be manufactured (in the form of a negative physical model), also based on the virtual soft model part 580, to provide mold surfaces that are substantially complementary to the outer-facing surfaces of the required soft model part 880. The mold can be manufactured using, for example via CNC material removal methods on a blank of suitable mold material and/or via a material additive process, for example a rapid prototyping manufacturing method, or any other suitable manufacturing method, using a suitably mold material, and using the appropriate machine instructions derived based on the virtual soft model part 580. The soft model part 880 can then be formed by casting or injecting suitable soft material into the mold and allowing to set. It is to be noted that the hard model part 860 can also be manufactured in a similar manner from a mold in the form of negative physical model that is based on the virtual hard model part 560 and manufactured based on and corresponding to the virtual hard model part 560, and using the appropriate machine instructions derived based thereon.

Alternatively, the soft model part 880 can be produced any other suitable computer-controlled manufacturing technique based on the virtual soft model part 580 and suitable relatively soft materials.

Referring to FIG. 14(*c*), the soft model part 880 is affixed onto the hard model part 860 to complete the composite physical model 800.

The soft model part 880 can be affixed onto the hard model part 860 in a number of different ways, for example via a mechanical arrangement, adhesives, welding and so on. For example, an interlocking mechanical arrangement can be provided, which is first modeled in the virtual soft model part 580 and/or the virtual hard model part 560.

For example, and as illustrated in FIGS. 14(*b*) and 14(*c*), in one such interlocking mechanical arrangement the soft model part 880 can be formed with a number of holes 885 that are configured for receiving complementary projections 865 formed on the hard model part 860 in corresponding locations, so that when thus received, the soft model part 880 is in the correct relative spatial relationship with respect to the hard model part 860. For example, the projections and holes can be formed integrally with the soft model part 880 and hard model part 860, and the corresponding virtual soft model part 580 and virtual hard model part 560 are correspondingly modified to include virtual of projections 585 and complementary virtual holes 565', respectively, in step 954 or in step 956, prior to manufacture. The projections and holes may have any cross-sectional shapes, so long as they are complementary to one another, and the projections may be formed as pins, tabs, and so on.

In alternative variations of this example, the holes can be formed on the hard model part 860 and the projections in the soft model part 880, or there can be a combination of projections and holes formed on the hard model part 860 that are paired to complementary holes and projections formed in the soft model part 880. Alternatively, holes can be formed on the hard model part 860 and in the soft model part 880, in mutual registry, and a plurality of pins used to connect paired holes in the hard model part 860 and the soft model part 880.

Alternatively, for example, suitable wells can be formed in corresponding parts of the soft model part 880 and hard model part 860, and suitable magnets placed in these wells so that the soft model part 880 and hard model part 860 can be engaged magnetically; the wells are first modeled in the corresponding virtual soft model part 580 and virtual hard model part 560.

Alternatively, for example, the soft model part 880 can be overlaid on hard model part 860, and affixed therein using spikes traversing the soft model part 880 and penetrating the hard model part 860, for example.

Alternatively, a suitable adhesive can be used for fixing the soft model part 880 on hard model part 860. In such a case, the soft model part 880 and/or hard model part 860, can be formed with a small clearance therebetween to allow room for the adhesive, and this clearance is first modeled in the virtual soft model part 580 and/or the virtual hard model part 560.

Alternatively, any other suitable means can be used for affixing the soft model part 880 to the hard model part 860, and modeled as appropriate in the virtual soft model part 580 and/or the virtual hard model part 560.

In any case, where appropriate, the virtual hard model part 560 and the virtual soft model part 580, can be formed with spatial virtual features that ensure that the corresponding physical features, formed on the hard model part 860 and the soft model part 880, respectively, provide (when aligned) the correct spatial disposition between the hard model part 860 and the soft model part 880. Such features may comprise suitable markings, for example.

Alternatively, in another example of steps 956 and 958, the composite physical model 800 can be made by first manufacturing the hard model part 860, for example as disclosed above, mutatis mutandis, and then the soft model part 880 can be subsequently formed in situ on the hard model part 860 of the composite physical model 800. For example, the virtual model 500 can be used to create a physical negative model of the composite physical model 800 to be used as a mold. The hard model part 860 is mounted in the physical negative model, and this results in a gap being created inbetween these two components, the gap corresponding to the soft model part 880. The soft model part 880 can then be formed by casting or injecting suitable soft material into this gap via suitable injection channels formed in the mold, for example, allowing the soft material to set as appropriate, and subsequently removing the physical negative model.

Alternatively, in another example of steps 956 and 958, a suitable rapid prototyping technique can be used for integrally forming the composite model 800, based on machine instructions derived from the virtual soft model part 580 and/or the virtual hard model part 560. For example an Objet rapid prototyping machine (for example as disclosed in website objet.com) can be used with two materials of different hardnesses, for example as marketed under "TANGO", which can be provided with different levels of rigidity. For parts of the composite physical model 800 corresponding to the virtual hard model part 560, the rapid prototyping machine uses a relatively hard material, while for parts of the composite physical model 800 corresponding to the virtual soft model part 580, the rapid prototyping machine uses a relatively soft material.

Figure 14C:
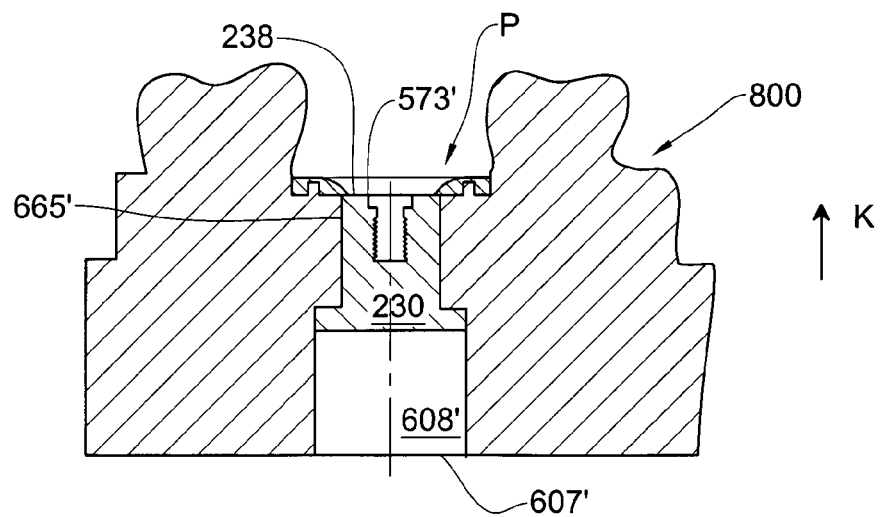

In at least this particular application of method 900 directed to the dental structure 100, and referring to FIG. 14(c), once the composite physical model 800 is ready, the analog 230 can be inserted into the composite model 800 in a general coronal direction K in a similar manner to that disclosed above for physical model 600, mutatis mutandis, to assume a spatial disposition P' that is fixed in six degrees of freedom with respect to the composite model 800, corresponding to the spatial disposition P of the implant 240 with respect to the dental structure 100. The prosthesis engaging part 238 of the analog 230 is thus surrounded by relatively soft material, for example in a similar manner to the implant 240 in the dental structure 100. In the installed position, the prosthesis engaging part 238 of the analog 230 is in abutment with the coronal opening 573' of the composite model 800, and thus the exposed part of the prosthesis engaging part 238 is visible and accessible via the coronal opening 573'.

In the above examples of implementation of method 900 with reference to dental model 100, step 950 also includes manufacturing the corresponding analog installation structure, as described herein with reference to the first aspect of the presently disclosed subject matter, mutatis mutandis.

It is to be noted that the composite physical model 800 can be formed with alignment features that allow the composite physical model 800 to be aligned with a physical model of the opposite jaw to provide proper occlusion, and/or be configured for mounting onto any dental articulator, in a similar manner to that described herein for physical model 600, mutatis mutandis.

According to the first aspect of the presently disclosed subject matter there is provided a system and method for manufacturing a physical model of a physical dental structure that includes a dental implant.

According to the first aspect of the presently disclosed subject matter there is also provided a method for creating a virtual model usable for making a physical model of a physical dental structure that includes a dental implant at an implant site, the method comprising:
  using a computer system:
    (a) receiving a virtual representation of dental surfaces of the physical dental structure with dental implant data representing a location and orientation of the dental implant with respect to the dental surfaces;
    (b) receiving a virtual analog structure, the virtual analog structure being based on said dental implant; and
    (c) creating the virtual model based on:
      said virtual representation of dental surfaces; and
      a virtual analog socket structure based on said virtual analog structure and said dental implant data, and having an virtual analog insertion opening that is spaced from parts of the virtual model corresponding to dental surfaces and the implant site.

The above method for creating a virtual model usable for making a physical model of a physical dental structure that includes a dental implant at an implant site, can optionally comprise one or more of the following features, in any desired combination or permutation:

(A) For example, said virtual analog structure is representative of a desired dental analog that corresponds to the dental implant, and wherein said virtual analog socket structure is configured for virtually receiving therein said analog virtual structure via said virtual analog insertion opening.
  (B) Additionally or alternatively for example, said virtual analog socket structure is configured for virtually receiving therein said analog virtual structure at a virtual installed position with respect to said virtual representation of dental surfaces corresponding to said implant data.
  (C) Additionally or alternatively for example, said virtual analog insertion opening is at a location other than at said virtual representation of dental surfaces.
  (D) Additionally or alternatively for example, said virtual analog insertion opening excludes a location in said virtual representation of dental surfaces corresponding to a location of the implant site in the physical dental structure.
  (E) Additionally or alternatively for example, said virtual analog insertion opening is different from an access opening to the virtual analog socket structure that is located at a location in said virtual representation of dental surfaces corresponding to a location of the implant site in the physical dental structure. For example, said access opening has a smaller maximum width than a maximum width of said virtual analog insertion opening.
  (F) Additionally or alternatively for example, step (a) further comprises receiving an auxiliary virtual representation of a base structure having base surfaces unrepresentative of said dental surfaces.
  (G) Alternatively for example, step (a) further comprises receiving an auxiliary virtual representation of a base structure having base surfaces unrepresentative of said dental surfaces, and for example, said virtual analog insertion opening is at a location in said virtual representation of dental surfaces corresponding to said base surface.
  (H) Additionally or alternatively for example, said virtual analog socket structure is configured for virtually receiving therein said analog virtual structure via said virtual analog insertion opening and along an insertion path, wherein said insertion path is along an insertion direction including at least one of:
    a general coronal direction;
    a non-apical direction;
    a direction passing through said virtual representation of dental surfaces from a first location with respect to the virtual model corresponding to an inside of the dental structure to a second location with respect to the virtual model corresponding to an outside of the dental structure.
  (I) Additionally or alternatively for example, step (a) comprises scanning the dental structure to generate said virtual representation of dental surfaces, and using a virtual implant part in said virtual representation of dental surfaces corresponding to an exposed part of the dental implant to obtain said dental implant data. For example, step (a) comprises comparing said virtual implant part to an implant virtual model representative of the dental implant, and operating on said virtual representation of dental surfaces to determine said dental implant data based on a location and orientation of said virtual implant part with respect to a remainder of said virtual representation of dental surfaces.

(J) Alternatively, for example, step (a) comprises:
performing a first scanning procedure of said dental structure with the dental implant exposed to generate said virtual representation of dental surfaces;
mounting a scanning abutment to the dental implant in an abutment spatial disposition with respect to the dental implant, performing a second scanning procedure of said dental structure including said scanning abutment to generate an auxiliary virtual model, and using a virtual scanning abutment part of the auxiliary virtual model corresponding to the scanning abutment to obtain said dental implant data.

(K) Additionally or alternatively for example, said virtual analog installation structure comprises a virtual passageway including said virtual analog insertion opening at one end thereof and an auxiliary opening at an opposed end thereof, said auxiliary opening corresponding to an interface between the dental implant and exposed dental surfaces of the dental structure in contact therewith. For example, said virtual passageway is elongate defining a virtual passageway longitudinal axis aligned with an insertion direction into said virtual passageway. Additionally or alternatively for example, said virtual passageway is formed comprising a virtual chamber having a form generally complementary to an external form of at least a part of the dental analog. Additionally or alternatively for example, at least a part of said virtual passageway is non-axisymmetric. Additionally or alternatively for example, said virtual passageway comprises a virtual stop configured for virtually abutting a corresponding part of said virtual analog structure for limiting virtual penetration of the virtual analog structure with respect to said virtual model. Additionally or alternatively for example, a significant virtual clearance gap is provided between said virtual passageway and said external form of at least a part of the dental analog.

(L) Additionally or alternatively for example, said virtual model is operated on to generate a virtual hard model part and a virtual soft model part, wherein said virtual hard model part corresponds to at least some hard tissues of the dental structure and wherein said virtual soft model part corresponds to at least some soft tissues of the dental structure. For example, said virtual soft model part corresponds to an area of the dental structure immediately adjacent the dental implant.

(M) Additionally or alternatively for example, the implant site is defined as an area enclosed by a perimeter defined as the interface between the dental surfaces and the dental implant.

(N) Additionally or alternatively for example, the method further comprises:
generating machine instructions for manufacturing the physical model based on said virtual model;
using the machine instructions, manufacturing the physical model, the physical model comprising a physical analog socket structure based on said virtual analog socket structure.

(O) Said differently, there is provided a method for making a physical model of a physical dental structure that includes a dental implant at an implant site, the method comprising:
providing a virtual model as defined above optionally including one or more of features (A) to (M) in any combination or combination;
generating machine instructions for manufacturing a physical model based on said virtual model;
using the machine instructions, manufacturing the physical model, the physical model comprising a physical analog socket structure based on said virtual analog socket structure.

(P) For example, said physical model is manufactured using one of a computer controlled material removal process and a computer controlled material additive process. For example: said computer controlled material removal process can be a CNC machining process; said computer controlled material additive process can be a rapid prototyping process.

(Q) For example, said physical model is manufactured having a substantially uniform hardness.

(R) Alternatively, for example, the physical model is manufactured having a hard model part and a soft model part. For example, said soft model part includes an area of said physical model immediately adjacent a opening thereof corresponding to said implant site and configured for exposing therethrough a prosthesis system engaging end of said dental analog when said dental analog is installed in the physical model. Additionally or alternatively for example, said soft model part corresponds to at least some soft tissues of said dental structure. Additionally or alternatively for example, said hard model part corresponds to at least some hard dental surfaces of said dental structure.

(S) For example, prior to manufacturing said physical model, said hard model part and said soft model part are first defined in said virtual model as a corresponding virtual hard model part and a corresponding virtual soft model part.

(T) Additionally or alternatively for example, the method for making a physical model of a physical dental structure that includes a dental implant at an implant site optionally further comprises:
providing the dental analog; and
inserting the dental analog into said physical model via said physical analog socket structure.

(U) A physical model, manufactured according to the method for making a physical model of a physical dental structure that includes a dental implant at an implant site (V) A kit comprising a physical model as defined above and at least one dental analog configured for use therewith by insertion into the physical model via said physical analog socket structure.

According to the first aspect of the presently disclosed subject matter there is also provided a method for creating a virtual model usable for making a physical model of a physical dental structure that includes a dental implant, the method comprising:
using a computer system:
(a) receiving a virtual representation of dental surfaces of the physical dental structure with dental implant data representing a location and orientation of the dental implant with respect to the dental surfaces, said dental surfaces including occlusal facing dental surfaces and adjacent dental side surfaces;
(b) receiving a virtual analog structure, the virtual analog structure being based on said dental implant; and
(c) creating the virtual model based on:
said virtual representation of dental surfaces; and
a virtual socket analog structure based on said virtual analog structure and said dental implant data, and having a virtual analog insertion opening at a location in said virtual representation of dental surfaces corresponding to said adjacent dental side surfaces of the dental surfaces.

For example, said adjacent dental side surfaces of the dental surfaces correspond to gingival tissues of the dental structure, and/or, said adjacent dental side surfaces of the dental surfaces correspond to tooth or prosthetic surfaces of the dental structure. Additionally or alternatively the method for creating a virtual model usable for making a physical model of a physical dental structure that includes a dental implant according to this aspect of the presently disclosed subject matter can optionally comprise one or more of features (A) to (F) and/or (H) to (V), mutatis mutandis, in any desired combination or permutation.

According to the first aspect of the presently disclosed subject matter there is also provided a method for creating a virtual model usable for making a physical model of a physical dental structure that includes a dental implant at an implant site, the method comprising:

using a computer system:
  (a) receiving a virtual representation of dental surfaces of the physical dental structure with dental implant data representing a location and orientation of the dental implant with respect to the dental surfaces;
  (b) receiving a virtual analog structure, the virtual analog structure being based on said dental implant; and
  (c) creating the virtual model based on:
    said first virtual representation of dental surfaces; and
    a virtual analog socket structure based on said virtual analog structure and said dental implant data, said virtual analog socket structure having a virtual analog insertion opening and an access opening at a location corresponding to the implant site, said access opening being different from said virtual analog insertion opening, wherein said access opening has a smaller maximum width than a maximum width of said virtual analog insertion opening.

For example, the virtual analog insertion opening is spaced from parts of the virtual model corresponding to dental surfaces and the implant site. Additionally or alternatively the method for creating a virtual model usable for making a physical model of a physical dental structure that includes a dental implant according to this aspect of the presently disclosed subject matter can optionally comprise one or more of features (A) to (D) and/or (F) to (V), mutatis mutandis, in any desired combination or permutation.

According to this aspect of the presently disclosed subject matter there is also provided a method for manufacturing a physical model of a physical dental structure that includes dental surfaces and a dental implant at an implant site, for use with a dental analog corresponding to the dental implant, the method comprising:

receiving a virtual model of the physical dental structure and a virtual analog installation structure in association with said virtual model, said virtual analog installation structure being based on the dental analog;

using said virtual model, manufacturing a physical model corresponding to said virtual model, the physical model being provided with an analog installation structure based on said virtual analog installation structure and thereby configured for enabling the dental analog to be inserted into said physical model through an insertion opening, wherein said insertion opening is spaced from a location in the physical model corresponding to the implant site in the physical dental structure.

The method optionally further comprises:
providing the dental analog; and
inserting said dental analog into said physical model via said analog installation structure, and fixing said dental analog therein at said analog spatial disposition.

Additionally or alternatively, for example, step (a) comprises scanning the dental structure to generate said virtual representation of dental surfaces, and using a virtual implant part in said virtual representation of dental surfaces corresponding to an exposed part of the dental implant to obtain said dental implant data. For example, step (a) comprises comparing said virtual implant part to an implant virtual model representative of the dental implant, and operating on said virtual representation of dental surfaces to determine said dental implant data based on a location and orientation of said virtual implant part with respect to a remainder of said virtual representation of dental surfaces.

Alternatively, for example, step (a) comprises:
performing a first scanning procedure of said dental structure with the dental implant exposed to generate said virtual representation of dental surfaces;
mounting a scanning abutment to the dental implant in an abutment spatial disposition with respect to the dental implant, performing a second scanning procedure of said dental structure including said scanning abutment to generate an auxiliary virtual model, and using a virtual scanning abutment part of the auxiliary virtual model corresponding to the scanning abutment to obtain said dental implant data.

Additionally or alternatively, for example, said virtual model comprises a virtual external surface corresponding to dental surfaces of said dental structure, and further comprising modifying said virtual model to include a virtual model base comprising a respective virtual external base surface. For example, said virtual external base surface excludes any representation of said dental surfaces of said dental structure. Additionally or alternatively, for example, in step (b) said analog installation structure is first defined in said virtual model as a virtual analog installation structure, said virtual analog installation structure comprising a virtual passageway having a first virtual opening provided in said virtual model base, and a second virtual opening corresponding to an interface between said dental implant and exposed dental tissues of said dental structure in contact therewith. For example, said virtual passageway is elongate defining a virtual passageway longitudinal axis aligned with said general coronal direction. Additionally or alternatively, for example, said virtual passageway is formed comprising a virtual chamber having a form generally complementary to an external form of at least a coronal part of said dental analog, such that a physical chamber corresponding to said virtual chamber and formed in said physical model provides a close fit with respect to at least said coronal part of said dental analog to accommodate said dental analog at said analog spatial disposition with respect to the physical model. Additionally or alternatively, for example, at least a part of said virtual passageway is non-axisymmetric. Additionally or alternatively, for example, said virtual passageway comprises a virtual stop corresponding to a mechanical stop in said physical model configured for limiting penetration of the dental analog to said installed position. Additionally or alternatively, for example, step (b) comprises aligning the virtual analog installation structure with said virtual model based on said virtual implant spatial disposition to ensure that said analog installation structure allows said analog to attain said analog spatial disposition in the physical model.

Additionally or alternatively, for example, said virtual passageway is formed comprising a virtual chamber having a form generally complementary to an external form of at least a coronal part of the dental analog, such that said chamber formed in said physical model provides a significant clearance gap with respect to said dental analog, wherein said dental analog comprises a jacket formed of suitable model material, said jacket having an external form substantially complementary to that of said chamber, to enable a composite analog comprising said dental analog including said jacket to be accommodated in said chamber at said analog spatial disposition.

Additionally or alternatively, for example, said virtual passageway comprises a virtual chamber having a form generally complementary to an external form of at least a coronal part of said dental analog, such that said chamber formed in said physical model provides a significant clearance gap with respect to said dental analog, and further comprising:
 maintaining said analog spatial disposition between said dental analog and said chamber using a jig at least until the dental analog is affixed therein;
 introducing a suitable filler into said clearance gap to fix said dental analog in said chamber at said analog spatial disposition.

Additionally or alternatively, for example, said insertion opening is at a location other than at physical model dental surfaces corresponding to said dental surfaces.

Additionally or alternatively, for example, said insertion opening excludes a location in said physical model corresponding to a location of the implant site in the dental structure.

Additionally or alternatively, for example, said insertion opening is different from an access opening to the analog installation structure that is located at a location in said physical model corresponding to a location of the implant site in the physical dental structure. For example, said access opening has a smaller maximum width than a maximum width of said insertion opening.

Additionally or alternatively, for example, herein said insertion path is along an insertion direction is at least one of
 a general coronal direction;
 a non-apical direction;
 a direction passing through a representation of said dental surfaces in the physical model, from a first location inside the physical model to a second location outside of the physical model.

Additionally or alternatively, for example, step (b) comprises:
 generating machine instructions for manufacturing the physical model based on said virtual model and the virtual analog installation structure;
 using the machine instructions, manufacturing the physical model.

Additionally or alternatively, for example, step (b) wherein said physical model is manufactured using one of a computer controlled material removal process and a computer controlled material additive process. For example: said computer controlled material removal process can be a CNC machining process; said computer controlled material additive process can be a rapid prototyping process.

Additionally or alternatively, for example, said physical model is manufactured having a substantially uniform hardness.

Alternatively, for example, the physical model is manufactured having a hard model part and a soft model part. For example, said soft model part includes an area of said physical model immediately adjacent a coronal opening thereof configured for exposing therethrough a coronal end of said dental analog when installed in the physical model. Additionally or alternatively, for example, said soft model part corresponds to at least some soft tissues of said dental structure. Additionally or alternatively, for example, said hard model part corresponds to at least some hard dental surfaces of said dental structure. Additionally or alternatively, for example, prior to manufacturing said physical model, said hard model part and said soft model part are first defined in said virtual model as a corresponding virtual hard model part and a corresponding virtual soft model part.

According to this aspect of the presently disclosed subject matter there is also provided a physical model, manufactured according to the method for making a physical model of a physical dental structure that includes a dental implant at an implant site According to this aspect of the presently disclosed subject matter there is also provided a kit comprising a physical model as defined above and at least one dental analog configured for use therewith by insertion into the physical model via said physical analog socket structure.

According to this aspect of the presently disclosed subject matter there is also provided a physical model of a dental structure, the dental structure including a dental implant at an implant site, the physical model being configured for enabling insertion therein of a dental analog corresponding to the dental implant via an insertion opening that is spaced from a model implant site location on the physical model corresponding to the implant site.

For example, the physical model is configured for enabling insertion therein of the dental analog to an installed position in a manner ensuring that a surface topology of said physical model in proximity to the dental analog in the installed position remain representative of the respective surface topology of the dental structure in the vicinity of the dental implant at least during said insertion. Additionally or alternatively, for example, the physical model comprises an analog installation structure configured for enabling the dental analog to be inserted therein via said insertion opening to said installed position therein having an analog spatial disposition with respect to said physical model corresponding to a physical implant spatial disposition of the dental implant with respect to the dental structure.

According to this aspect of the presently disclosed subject matter there is also provided a said physical model comprises an external surface corresponding to dental surfaces of the dental structure, and further comprises a model base comprising a respective external base surface. For example, said external base surface excludes any representation of the dental surfaces of the dental structure. Additionally or alternatively, for example, said analog installation structure comprising a passageway extending from said insertion opening provided in said model base, and a second opening on said external surface at said model implant site location. For example, said passageway is elongate defining a passageway longitudinal axis aligned with a general coronal direction. For example, said passageway longitudinal axis is co-axial with a longitudinal axis of the dental analog when the dental analog is in said installed position. Additionally or alternatively, for example, said passageway comprises a chamber having a form generally complementary to an external form of at least a coronal part of the dental analog, such that said physical chamber provides a close fit with respect to at least said coronal part of the dental analog to accommodate the dental analog at said analog spatial disposition with respect to the physical model. Additionally or alternatively, for example, said passageway comprises a chamber having a form generally complementary to an external form of at least a coronal part of said dental analog, such that said chamber formed provides a significant clearance gap with respect to said dental analog. Additionally or alternatively, for example, at least a part of said passageway is non-axisymmetric. Additionally or alternatively, for example, said passageway comprises a mechanical stop configured for limiting penetration of the dental analog to said installed position.

Additionally or alternatively, for example, said physical model comprises a uniform hardness.

Alternatively, for example, the physical model comprises a hard model part and a soft model part. For example, said soft model part includes an area of said physical model adjacent a second opening thereof configured for exposing therethrough a coronal end of said dental analog when installed in the physical model. Additionally or alternatively, for example, said soft model part corresponds to at least some soft tissues of the dental structure. Additionally or alternatively, for example, said hard model part corresponds to at least some hard dental surfaces of the dental structure.

Additionally or alternatively, for example, the implant site corresponds to an interface between the dental implant and exposed dental tissues of the dental structure in contact therewith Additionally or alternatively, for example, said second opening has a smaller maximum width than a maximum width of said insertion opening.

According to this aspect of the presently disclosed subject matter there is also provided a dental analog configured for being inserted into a passageway of a physical model of a dental structure, which dental structure includes a dental implant at an implant site, the passageway including an insertion opening and a second opening corresponding to the implant site, said second opening having a smaller maximum width than a maximum width of said insertion opening. For example, the dental analog comprises a first analog end corresponding to said insertion opening and a second analog end corresponding to said second opening, wherein said second analog end has a smaller maximum width than a maximum width of said first analog end.

Additionally or alternatively, for example, the dental analog has a coronal portion and an enlarged apical portion, wherein in use said dental analog is implanted in a physical model of a dental structure in an installed position such that said coronal portion and said enlarged apical portion are within the physical model.

Additionally or alternatively, for example, the dental analog comprises a longitudinal axis, and wherein at least a longitudinal portion of one of said coronal portion and an apical portion is non-axisymmetric about said longitudinal axis.

Additionally or alternatively, for example, the dental analog comprises an external form configured for being inserted into the physical dental model in a general coronal direction to the installed position via the passageway formed in the physical model, wherein at least a portion of said external form is non-axisymmetric with respect to said general coronal direction. For example, at least one of said coronal portion and said apical portion is configured for fixing a spatial disposition of the dental analog with respect to the passageway in up to four degrees of freedom associated with axes orthogonal to the general coronal direction.

Additionally or alternatively, for example, said enlarged apical portion acts as a mechanical stop with respect to a corresponding part of the passageway to define the longitudinal position of said dental analog with respect to the passageway.

Additionally or alternatively, for example, said dental analog comprises a prosthesis interface analog part and a prosthesis engaging analog part respectively corresponding to a prosthesis interface implant part and prosthesis engaging implant part of respective dental implant, wherein the dental implant is chosen from a plurality of dental implant configurations having different configurations for the respective said prosthesis interface implant part and said prosthesis engaging implant part.

According to this aspect of the presently disclosed subject matter there is also provided a kit comprising a physical model of a dental structure that includes a dental implant at an implant site, the physical model having a passageway, an insertion opening and a second opening corresponding to the implant site, said second opening smaller maximum width than a maximum width of said insertion opening and at least one dental analog as defined above.

According to the first aspect of the presently disclosed subject matter there is also provided a system and method for manufacturing a physical model of a dental structure that includes a dental implant. In at least one example, the physical model is configured to allow a dental analog can be inserted into the physical model in a general coronal direction. A virtual model of the dental structure is provided including a virtual implant spatial disposition with respect to the virtual model corresponding to a physical implant spatial disposition of the dental implant with respect to the physical dental structure. A virtual analog installation structure is defined in the virtual model. Using the virtual model, a physical model corresponding to the virtual model is manufactured, the physical model being provided with a physical analog installation structure corresponding to the virtual analog installation structure. The physical analog installation structure is configured for enabling a dental analog, corresponding to the dental implant, to be inserted in a general coronal direction with respect to the physical model to an installed position in the physical model. In the installed position, the dental analog has an analog spatial disposition with respect to the physical model corresponding to the physical implant spatial disposition of the dental implant with respect to the physical dental structure.

According to the second aspect of the presently disclosed subject matter there is provided a system and method for manufacturing a composite physical dental model of a dental structure, the method broadly comprising:

(a) providing a virtual model of the dental structure;
(b) using said virtual model, manufacturing a composite physical model corresponding to said virtual model, the physical model including a first model part and a second model part having at least one physical property different from a physical property of said first model part, wherein said first model part and said second model part are previously defined in said virtual model, and wherein said at least one physical property excludes a surface topology.

For example said physical property is a mechanical property.

For example, step (b) comprises:
(b1) identifying at least some virtual surfaces of said virtual model corresponding to at least a part of the soft dental surfaces of the dental structure;

(b2) modifying said virtual model to create a first virtual model part corresponding to said at least part of the soft dental surfaces, and a second virtual model part corresponding to at least a part of the hard dental surfaces of the dental structure.

For example, step (b) further comprises:

(b3) generating machine instructions for manufacturing the physical composite model including said first model part based on and corresponding to said first virtual model part and said second model part based on and corresponding to said second virtual model part;

(b4) using the machine instructions, manufacturing the physical composite model.

Additionally or alternatively, said virtual model comprises a virtual surface corresponding to a dental surface of said dental structure, wherein said first virtual model part includes a first virtual surface part of said virtual surface and wherein said second virtual model part includes a second virtual surface part of said virtual surface. For example, said first virtual surface part is in virtual abutment with said second virtual surface part.

Additionally or alternatively, in step (b4), said first model part is produced separately from said second model part, and wherein said first model part and model part are joined together in said composite model. For example, said second physical model part is produced using one of a computer controlled material removal process and a computer controlled material additive process: for example, the computer controlled material removal process is a CNC machining process; for example the computer controlled material additive process is a rapid prototyping procedure. For example, said first physical model part is produced by a separate casting procedure or via a rapid prototyping procedure.

For example, said first physical model part and said second physical model part are produced with affixing features configured for enabling the first physical model part to be affixed with respect to the second physical model part in a relative spatial disposition therewith corresponding to the relative spatial disposition of the respective real parts of the real dental structure. For example, said affixing features correspond to virtual affixing features previously defined in said first virtual model part and said second virtual model part in step (b).

Alternatively, in step (b4), said second model part is produced first, and said first model part is produced in situ on said second model part. For example, said second physical model part is produced using one of a computer controlled material removal process and a computer controlled material additive process, and wherein said first physical model part is produced by a casting procedure Alternatively, in step (b4), said first model part is produced integrally with said second model part. For example, said first model part and said second model part are integrally produced via a computer controlled material additive process, for example a rapid prototyping procedure. For example, said rapid prototyping procedure employs a first material for producing said first model part, and a second material for producing said second model part, said first material and said second material being of a different said property one from another. For example, said first material is relatively softer than said second material.

Additionally or alternatively, said at least one physical property is chosen from texture, resilience, color and softness.

Additionally or alternatively, said composite model is further configured with alignment features for enabling occlusal alignment of the composite physical model with a physical dental model of an opposite jaw.

Additionally or alternatively, the dental structure includes a dental implant, and wherein said composite model is configured for installing therein a corresponding dental analog. For example, said first model part includes an area of said composite model adjacent a coronal opening thereof configured for exposing therethrough a coronal end of the dental analog when installed in the composite model. For example such a composite model can further assist a dental technician in the design and/or preparation of the permanent abutment, coping, prosthesis and so on.

A composite physical dental model is also provided, produced with the respective method as defined above.

According to this aspect of the presently disclosed subject matter, before manufacturing the composite model, the soft model part and the hard model part are defined as virtual models.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed example examples in accordance with the presently disclosed subject matter, it will be appreciated that many changes can be made therein without departing from the spirit of the presently disclosed subject matter.

The invention claimed is:

1. A method for creating a virtual model usable for making a physical model of a physical dental structure that includes a dental implant at an implant site, the method comprising:
  (a) receiving, on a computer system, a virtual representation of dental surfaces of the physical dental structure and dental implant data representing a location and orientation of the dental implant with respect to the dental surfaces;
  (b) receiving, on the computer system, a virtual analog structure, the virtual analog structure being based on said dental implant; and
  (c) creating, on the computer system, the virtual model based on:
  said virtual representation of dental surfaces; and
  a virtual analog socket structure based on said virtual analog structure and said dental implant data, said virtual analog socket structure having a coronal opening and a virtual analog insertion opening on respective ends thereof, wherein:
  the coronal opening corresponds to an interface between the dental implant and exposed dental surfaces of the dental structure in contact therewith,
  the virtual analog insertion opening is spaced apart from the coronal opening and parts of the virtual model corresponding to dental surfaces and the implant site, and
  the virtual analog socket structure is shaped to virtually receive therein said virtual analog structure along an insertion path entering into said virtual analog socket structure via said virtual analog insertion opening,
  wherein the analog socket structure comprises a coronal portion, an apical portion, and a shoulder at an interface between the coronal portion and the apical portion, the coronal portion extending from the coronal opening to the shoulder and the apical portion extending from the virtual analog insertion opening to the shoulder, the shoulder being orientated away from the coronal opening and complementary to a face of the virtual analog structure.

2. The method according to claim 1, wherein said virtual analog structure is representative of a desired dental analog that corresponds to the dental implant.

3. The method according to claim 1, wherein said virtual analog socket structure is configured for virtually receiving therein said virtual analog structure at a virtual installed position with respect to said virtual representation of dental surfaces corresponding to said implant data.

4. The method according to claim 1 wherein said virtual analog insertion opening is at a location other than at said virtual representation of dental surfaces.

5. The method according to claim 1, wherein said virtual analog insertion opening is different from an access opening to the virtual analog socket structure that is located at a location in said virtual representation of dental surfaces corresponding to a location of the implant site in the physical dental structure.

6. The method according to claim 5, wherein said access opening has a smaller maximum width than a maximum width of said virtual analog insertion opening.

7. The method according to claim 1, wherein step (a) further comprises receiving an auxiliary virtual representation of a base structure having base surfaces unrepresentative of said dental surfaces.

8. The method according to claim 7, wherein said virtual analog insertion opening is at a location in said virtual representation of dental surfaces corresponding to said base surface.

9. The method according to claim 1, wherein said virtual analog socket structure is configured for virtually receiving therein said virtual analog structure along said insertion path, wherein said insertion path is along an insertion direction including at least one of:
   a general coronal direction;
   a non-apical direction; and
   a direction passing through said virtual representation of dental surfaces from a first location with respect to the virtual model corresponding to an inside of the dental structure to a second location with respect to the virtual model corresponding to an outside of the dental structure.

10. The method according to claim 1, wherein the method comprises receiving scan data of the dental structure to generate said virtual representation of dental surfaces, and using a virtual implant part in said virtual representation of dental surfaces corresponding to an exposed part of the dental implant to obtain said dental implant data.

11. The method according to claim 10, comprising comparing said virtual implant part to an implant virtual model representative of the dental implant, and operating on said virtual representation of dental surfaces to determine said dental implant data based on a location and orientation of said virtual implant part with respect to a remainder of said virtual representation of dental surfaces.

12. The method according to claim 1, wherein the method comprises:
   performing receiving scan data from a first scanning procedure of said dental structure with the dental implant exposed to generate said virtual representation of dental surfaces;
   mounting a scanning abutment to the dental implant in an abutment spatial disposition with respect to the dental implant, receiving scan data from a second scanning procedure of said dental structure, the scan data from the second scanning procedure including a scanning abutment mounted to the dental implant in abutment spatial disposition with respect to the dental implant thereby generating an auxiliary virtual model, and using a virtual scanning abutment part of the auxiliary virtual model corresponding to the scanning abutment to obtain said dental implant data.

13. The method according to claim 1, wherein said virtual analog installation structure comprises a virtual passageway including said virtual analog insertion opening at one end thereof and said coronal opening at an opposed end thereof.

14. The method according to claim 13, wherein said virtual passageway is elongate defining a virtual passageway longitudinal axis aligned with an insertion direction into said virtual passageway.

15. The method according to claim 13, wherein said virtual passageway is formed comprising a virtual chamber having a form generally complementary to an external form of at least a part of the dental analog.

16. The method according to claim 15, wherein a virtual clearance gap is provided between said virtual passageway and said external form of at least a part of the dental analog.

17. The method according to claim 13, wherein at least a part of said virtual passageway is non-axisymmetric.

18. The method according to claim 13, wherein said virtual passageway comprises a virtual stop configured for virtually abutting a corresponding part of said virtual analog structure for limiting virtual penetration of the virtual analog structure with respect to said virtual model.

19. The method according to claim 1, wherein said virtual model includes a virtual hard model part and a virtual soft model part, wherein said virtual hard model part corresponds to at least some hard tissues of the dental structure and wherein said virtual soft model part corresponds to at least some soft tissues of the dental structure.

20. The method according to claim 19, wherein said virtual soft model part corresponds to an area of the dental structure immediately adjacent the dental implant.

21. The method according to claim 1, wherein the implant site is defined as an area enclosed by a perimeter defined as the interface between the dental surfaces and the dental implant.

22. The method according to claim 1, further comprising:
   generating machine instructions for manufacturing the physical model based on said virtual model;
   outputting the machine instructions for manufacturing the physical model, the physical model comprising a physical analog socket structure based on said virtual analog socket structure.

* * * * *